(12) United States Patent
Goto et al.

(10) Patent No.: US 8,637,125 B2
(45) Date of Patent: Jan. 28, 2014

(54) LIQUID CRYSTAL COMPOSITION AND LIQUID CRYSTAL DISPLAY DEVICE

(75) Inventors: Yasuyuki Goto, Tokyo (JP); Subaru Kawasaki, Chiba (JP); Norikatsu Hattori, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 6 days.

(21) Appl. No.: 13/444,868

(22) Filed: Apr. 12, 2012

(65) Prior Publication Data

US 2012/0261614 A1   Oct. 18, 2012

(30) Foreign Application Priority Data

Apr. 18, 2011  (JP) ................. 2011-092212

(51) Int. Cl.
| | |
|---|---|
| C09K 19/34 | (2006.01) |
| C09K 19/30 | (2006.01) |
| C09K 19/32 | (2006.01) |
| C09K 19/12 | (2006.01) |
| C09K 19/20 | (2006.01) |
| C07C 22/02 | (2006.01) |

(52) U.S. Cl.
USPC .. 428/1.1; 570/131; 252/299.01; 252/299.61; 252/299.62; 252/299.63; 252/299.66; 252/299.67

(58) Field of Classification Search
CPC ................................... C07C 49/807
USPC ........... 428/1.1; 252/299.61, 299.62, 299.63, 252/299.66, 299.67, 299.01; 570/131
See application file for complete search history.

(56) References Cited

U.S. PATENT DOCUMENTS 5,308,537 A * 5/1994 Coates et al. .............. 252/299.6
5,779,936 A * 7/1998 Miyazawa et al. ....... 252/299.63

FOREIGN PATENT DOCUMENTS

| JP | H11-035500 | 2/1999 |
| WO | 90/13610 | 11/1990 |

* cited by examiner

Primary Examiner — Shean C Wu
(74) Attorney, Agent, or Firm — Jianq Chyun IP Office

(57) ABSTRACT

Providing a liquid crystal composition satisfying at least one of characteristics such as high maximum temperature of nematic phase, low minimum temperature of the nematic phase, small viscosity, suitable optical anisotropy, large negative dielectric anisotropy, large specific resistance, high stability to ultraviolet light and heat, or having a suitable balance regarding at least two of the characteristics; and an AM device having short response time, large voltage holding ratio, large contrast ratio, long service life and so forth. The liquid crystal composition has a negative dielectric anisotropy and contains a specific two-ring compound having a low minimum temperature as a first component, a specific compound having a large negative dielectric anisotropy as a second component, a specific compound having a low viscosity as a third component, and a specific compound having a large negative dielectric anisotropy as a fourth component. The liquid crystal display device contains the composition.

16 Claims, No Drawings

LIQUID CRYSTAL COMPOSITION AND LIQUID CRYSTAL DISPLAY DEVICE

CROSS-REFERENCE TO RELATED APPLICATION

This application claims the priority benefit of Japan application serial no. 2011-092212, filed on Apr. 18, 2011. The entirety of the above-mentioned patent application is hereby incorporated by reference herein and made a part of this specification.

TECHNICAL FIELD

The invention relates to a liquid crystal composition mainly suitable for use in an active matrix (AM) device and so forth, and an AM device and so forth containing the composition. More specifically, the invention relates to a liquid crystal composition having a negative dielectric anisotropy, and a device that contains the composition and has a mode such as an in-plane switching (IPS) mode, a vertical alignment (VA) mode, a fringe field switching (FFS) mode or a polymer sustained alignment (PSA) mode.

BACKGROUND ART

In a liquid crystal display device, a classification based on an operating mode for liquid crystals includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode. A classification based on a driving mode in the device includes a passive matrix (PM) and an active matrix (AM). The PM is further classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transreflective type utilizing both the natural light and the backlight.

The devices contain a liquid crystal composition having suitable characteristics. The liquid crystal composition has a nematic phase. General characteristics of the composition should be improved to obtain an AM device having good general characteristics. Table 1 below summarizes a relationship between two of the general characteristics. The general characteristics of the composition will be explained further based on a commercially available AM device. A temperature range of the nematic phase relates to a temperature range in which the device can be used. A preferred maximum temperature of the nematic phase is approximately 70° C. or higher and a preferred minimum temperature of the nematic phase is approximately −20° C. or lower. Viscosity of the composition relates to a response time in the device. A short response time is preferred for displaying moving images on the device. Accordingly, a small viscosity in the composition is preferred. A small viscosity at a low temperature is further preferred.

TABLE 1

General Characteristics of Composition and AM Device

| No. | General Characteristics of Composition | General Characteristics of AM Device |
| --- | --- | --- |
| 1 | wide temperature range of a nematic phase | wide usable temperature range |
| 2 | small viscosity[1] | short response time |
| 3 | suitable optical anisotropy | large contrast ratio |
| 4 | large positive or negative dielectric anisotropy | low threshold voltage and small electric power consumption large contrast ratio |
| 5 | large specific resistance | large voltage holding ratio and large contrast ratio |
| 6 | high stability to ultraviolet light and heat | long service life |

[1] A liquid crystal composition can be injected into a liquid crystal cell in a shorter period of time.

An optical anisotropy of the composition relates to a contrast ratio in the device. A product (Δn×d) of the optical anisotropy (Δn) of the composition and a cell gap (d) in the device is designed so as to maximize the contrast ratio. A suitable value of the product depends on a type of the operating mode. The suitable value is in the range of approximately 0.30 micrometer to approximately 0.40 micrometer in a device having the VA mode, and in the range of approximately 0.20 micrometer to approximately 0.30 micrometer in a device having the IPS mode or the FFS mode. In the above case, a composition having a large optical anisotropy is preferred for a device having a small cell gap. A large absolute value of a dielectric anisotropy in the composition contributes to a low threshold voltage, a small electric power consumption and a large contrast ratio in the device. Accordingly, the large absolute value of the dielectric anisotropy is preferred. A large specific resistance in the composition contributes to a large voltage holding ratio and a large contrast ratio in the device. Accordingly, a composition having a large specific resistance, at room temperature and also at a high temperature in an initial stage, is preferred. A composition having a large specific resistance, at room temperature and also at a high temperature after the device has been used for a long period of time, is preferred. Stability of the composition to ultraviolet light and heat relates to a service life of the liquid crystal display device. In the case where the stability is high, the device has a long service life. Such characteristics are preferred for an AM device used in a liquid crystal projector, a liquid crystal television and so forth.

A composition having a positive dielectric anisotropy is used for an AM device having the TN mode. On the other hand, a composition having a negative dielectric anisotropy is used for an AM device having the VA mode. A composition having a positive or negative dielectric anisotropy is used for an AM device having the IPS mode or the FFS mode. A composition having a positive or negative dielectric anisotropy is used for an AM device having the PSA mode. Examples of the liquid crystal composition are disclosed in Patent literatures No. 1 and No. 2 as described below.

CITATION LIST

Patent Literature

Patent literature No. 1: JP H11-035500 A.
Patent literature No. 2: JP H3-505742 A.

A desirable AM device has characteristics such as a wide temperature range in which a device can be used, a short response time, a large contrast ratio, a low threshold voltage, a large voltage holding ratio and a long service life. A shorter response time even by one millisecond is desirable. Thus, desirable characteristics of a composition include a high maximum temperature of a nematic phase, a low minimum temperature of the nematic phase, a small viscosity, a suitable optical anisotropy, a large positive or negative dielectric anisotropy, a large specific resistance, a high stability to ultraviolet light and a high stability to heat.

SUMMARY OF INVENTION

The inventors of the invention have diligently continued to conduct research for solving the problem, as a result, have found that a specific liquid crystal composition satisfies desirable characteristics and a liquid crystal display device containing the composition exhibits an excellent performance, and thus has completed the invention based on the knowledge.

The invention concerns a liquid crystal composition that has a negative dielectric anisotropy and contains a specific compound as a first component and a specific compound as a second component.

The invention further concerns a liquid crystal display device containing the composition.

The invention still further concerns use of the liquid crystal composition in the liquid crystal device.

Technical Problem

One of the aims of the invention is to provide a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another aim is to provide a liquid crystal composition having a suitable balance regarding at least two of the characteristics, in particular, a liquid crystal composition satisfying the low minimum temperature and the large negative dielectric anisotropy. A further aim is to provide a liquid crystal display device containing such a composition. An additional aim is to provide a composition having a suitable optical anisotropy to be a small optical anisotropy or a large optical anisotropy, a large negative dielectric anisotropy, a high stability to ultraviolet light and so forth, and is to provide an AM device having characteristics such as a short response time, a large voltage holding ratio, a large contrast ratio and a long service life.

Solution to Problem

The invention concerns a liquid crystal composition that has a negative dielectric anisotropy and contains at least one compound selected from the group of compounds represented by formula (1) as a first component and at least one compound selected from the group of compounds represented by formula (2) as a second component, and concerns a liquid crystal display device containing the composition:

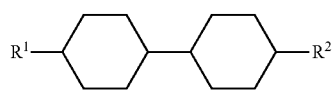
(1)

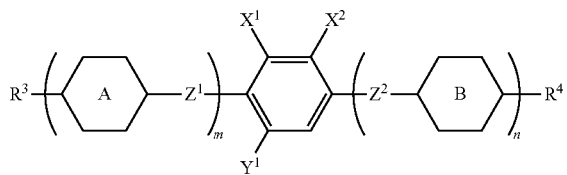

wherein $R^1$ is alkyl having 1 to 12 carbons in which one or two of hydrogen are replaced by fluorine; $R^2$, $R^3$ and $R^4$ are independently alkyl having 1 to 12 carbons, alkoxy having 1 to 12 carbons or alkenyl having 2 to 12 carbons; ring A and ring B are independently

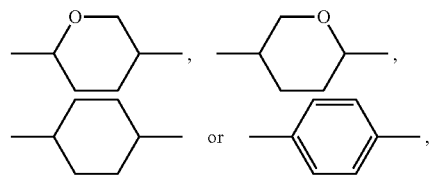

$X^1$ and $X^2$ are independently fluorine or chlorine; $Y^1$ is hydrogen or methyl; $Z^1$ and $Z^2$ are independently a single bond, ethylene, methyleneoxy or carbonyloxy; and m and n are independently 0, 1, 2 or 3, and a sum of m and n is 1, 2 or 3.

Advantageous Effects of Invention

An advantage of the invention is a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. One aspect of the invention is a liquid crystal composition having a suitable balance regarding at least two of the characteristics. Another aspect is a liquid crystal display device containing such a composition. A further aspect is a composition having a suitable optical anisotropy, a large negative dielectric anisotropy, a high stability to ultraviolet light and so forth, and is an AM device having a short response time, a large voltage holding ratio, a large contrast ratio, a long service life and so forth.

DESCRIPTION OF EMBODIMENTS

Usage of terms in the specification and claims is as described below. A liquid crystal composition or a liquid crystal display device of the invention may be abbreviated as "composition" or "device," respectively. The liquid crystal display device is a generic term for a liquid crystal display panel and a liquid crystal display module. "Liquid crystal compound" means a compound having a liquid crystal phase such as a nematic phase or a smectic phase, or a compound having no liquid crystal phase but being useful as a component of the composition. Such a useful compound has a six-membered ring such as 1,4-cyclohexylene and 1,4-phenylene, and a rod-like molecular structure. An optically active compound and a polymerizable compound may occasionally be added to the composition. Even in the case where the compounds are liquid crystalline, the compounds are classified as an additive herein. At least one compound selected from the group of compounds represented by formula (1) may be abbreviated as "compound (1)." "Compound (1)" means one compound or two or more compounds represented by formula (1). A same rule applies to any other compound represented by any other formula. "At least one" when "replaced" means that not only positions but also numbers of replacement may be freely selected.

A higher limit of a temperature range of the nematic phase may be abbreviated as "maximum temperature." A lower limit of the temperature range of the nematic phase may be abbreviated as "minimum temperature." An expression "a specific resistance is large" means that the composition has a large specific resistance at room temperature and also at a temperature close to the maximum temperature of the nematic phase in an initial stage, and that the composition has a large specific resistance at room temperature and also at a temperature close to the maximum temperature of the nematic phase even after the device has been used for a long period of time. An expression "a voltage holding ratio is large" means that the device has a large voltage holding ratio at room temperature and also at a temperature close to the maximum temperature of the nematic phase in an initial stage, and that the device has a large voltage holding ratio at room temperature and also at a temperature close to the maximum temperature of the nematic phase even after the device has been used for a long period of time. When characteristics such as an optical anisotropy are explained, values obtained according to the measuring methods described in Examples will be used. The first component includes one compound or two or more compounds. A term "a ratio of the first component" is expressed in terms of weight percent (% by weight) of the first component based on the total weight of the liquid crystal composition. A same rule applies to a ratio of the second component and so forth. A ratio of the additive mixed with the composition is expressed in terms of weight percent (% by weight) or weight parts per million (ppm) based on the total weight of the liquid crystal composition.

A symbol $R^2$ is used for a plurality of compounds in chemical formulas of component compounds. A group to be selected by $R^2$ may be identical or different in two of arbitrary compounds among the plurality of the compounds. In one case, for example, $R^2$ of compound (1) is ethyl and $R^2$ of compound (1-1) is ethyl. In another case, $R^2$ of compound (1) is ethyl and $R^2$ of compound (1-1) is propyl. A same rule applies to a symbol $R^3$, $R^4$ or the like.

The invention includes the items described below.

Item 1. A liquid crystal composition that has a negative dielectric anisotropy and contains at least one compound selected from the group of compounds represented by formula (1) as a first component and at least one compound selected from the group of compounds represented by formula (2) as a second component:

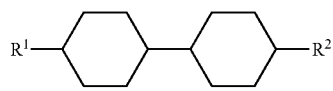

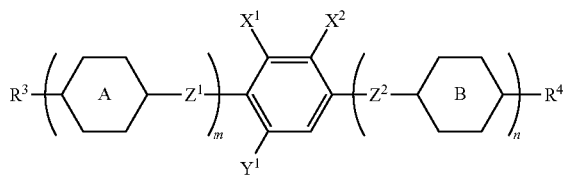

wherein $R^1$ is alkyl having 1 to 12 carbons in which one or two of hydrogen are replaced by fluorine; $R^2$, $R^3$ and $R^4$ are independently alkyl having 1 to 12 carbons, alkoxy having 1 to 12 carbons or alkenyl having 2 to 12 carbons; ring A and ring B are independently

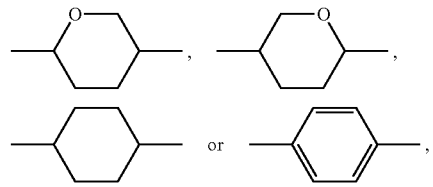

$X^1$ and $X^2$ are independently fluorine or chlorine; $Y^1$ is hydrogen or methyl; $Z^1$ and $Z^2$ are independently a single bond, ethylene, methyleneoxy or carbonyloxy; and m and n are independently 0, 1, 2 or 3, and a sum of m and n is 1, 2 or 3.

Item 2. The liquid crystal composition according to item 1, wherein the first component contains at least one compound selected from the group of compounds represented by formula (1-1):

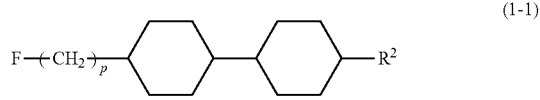

wherein $R^2$ is alkyl having 1 to 12 carbons, alkoxy having 1 to 12 carbons or alkenyl having 2 to 12 carbons; and p is an integer from 1 to 12.

Item 3. The liquid crystal composition according to item 1 or 2, wherein the second component is at least one compound selected from the group of compounds represented by formula (2-1) to formula (2-12):

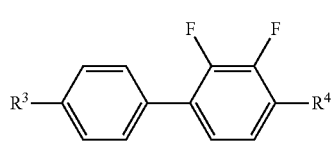

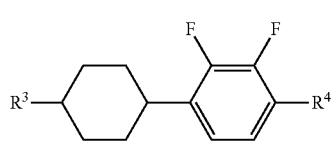

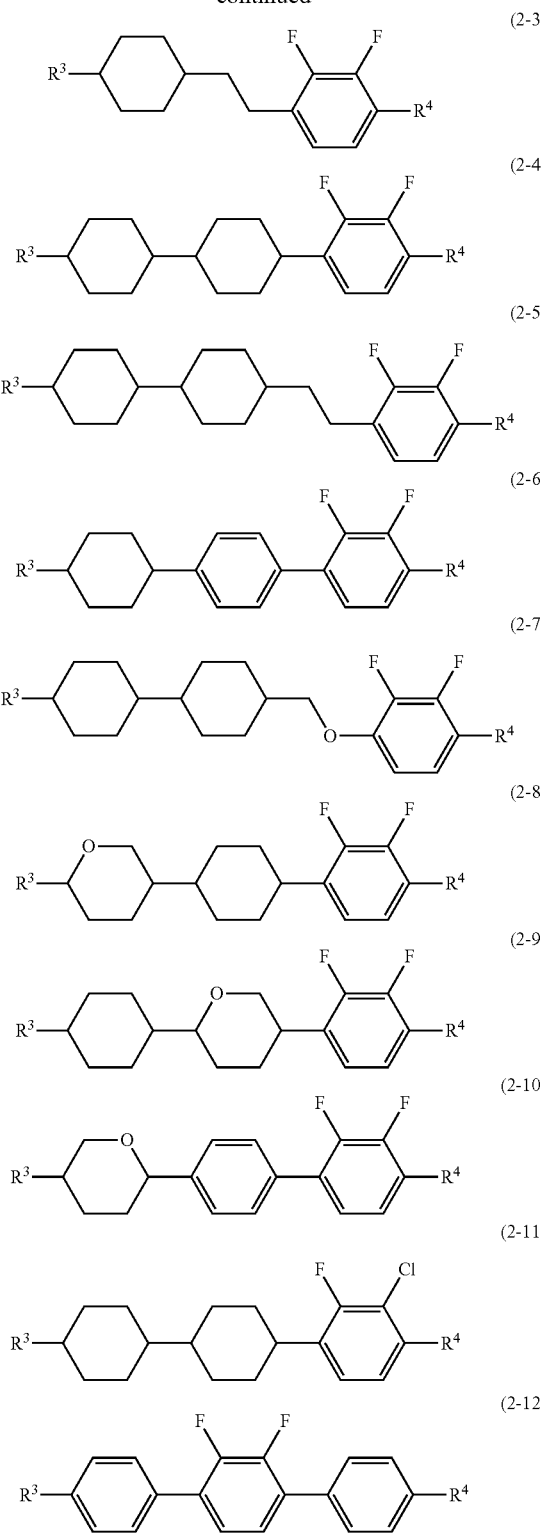

wherein $R^3$ and $R^4$ are independently alkyl having 1 to 12 carbons, alkoxy having 1 to 12 carbons or alkenyl having 2 to 12 carbons.

Item 4. The liquid crystal composition according to item 2, wherein the second component is at least one compound selected from the group of compounds represented by formula (2-1) according to item 3.

Item 5. The liquid crystal composition according to item 2, wherein the second component is at least one compound selected from the group of compounds represented by formula (2-4) according to item 3.

Item 6. The liquid crystal composition according to item 2, wherein the second component is at least one compound selected from the group of compounds represented by formula (2-6) according to item 3.

Item 7. The liquid crystal composition according to item 2, wherein the second component is at least one compound selected from the group of compounds represented by formula (2-7) according to item 3.

Item 8. The liquid crystal composition according to item 2, wherein the second component is at least one compound selected from the group of compounds represented by formula (2-9) according to item 3.

Item 9. The liquid crystal composition according to any one of items 1 to 8, wherein a ratio of the first component is in the range of 5% by weight to 80% by weight and a ratio of the second component is in the range of 10% by weight to 95% by weight based on the total weight of the liquid crystal composition.

Item 10. The liquid crystal composition according to any one of items 1 to 9, further containing at least one compound selected from the group of compounds represented by formula (3) as a third component:

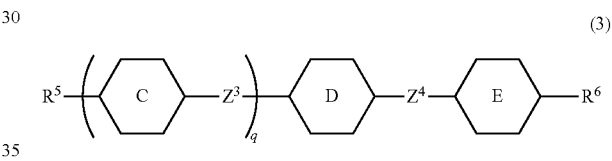

(3)

wherein $R^5$ and $R^6$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine; ring C, ring D and ring E are independently 1,4-cyclohexylene, 1,4-phenylene, 2-fluoro-1,4-phenylene or 3-fluoro-1,4-phenylene; $Z^3$ and $Z^4$ are independently a single bond, ethylene, methyleneoxy or carbonyloxy; and q is 0, 1 or 2.

Item 11. The liquid crystal composition according to item 10, wherein the third component is at least one compound selected from the group of compounds represented by formula (3-1) to formula (3-13):

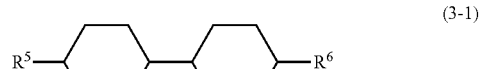

(3-1)

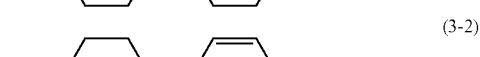

(3-2)

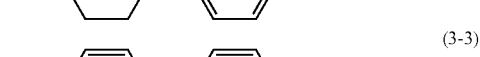

(3-3)

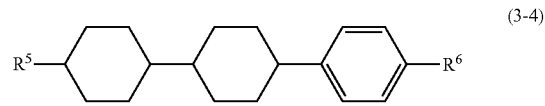

(3-4)

-continued

(3-5)

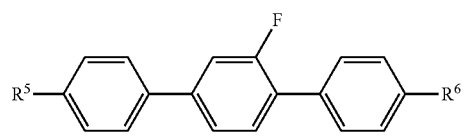
(3-6)

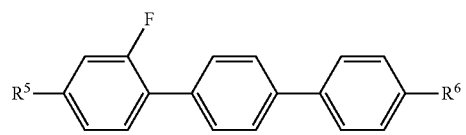
(3-7)

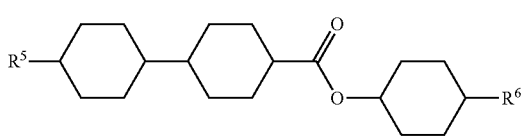
(3-8)

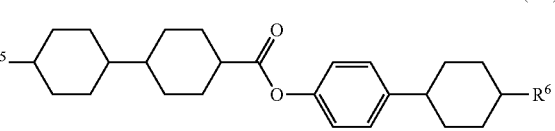
(3-9)

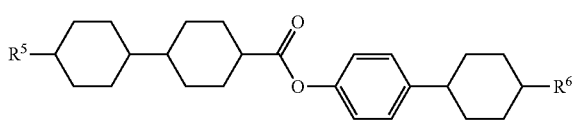
(3-10)

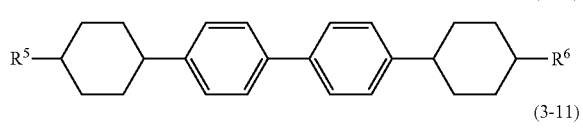
(3-11)

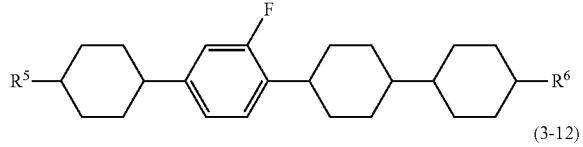
(3-12)

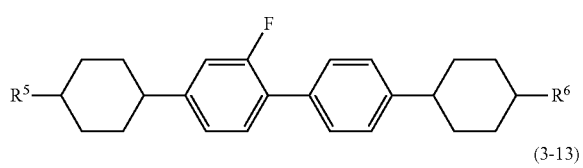
(3-13)

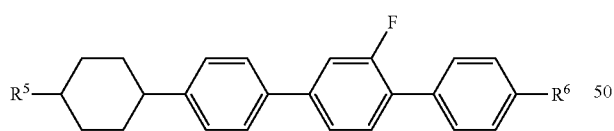

wherein $R^5$ and $R^6$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine.

Item 12. The liquid crystal composition according to item 10, wherein the third component is at least one compound selected from the group of compounds represented by formula (3-1) according to item 11.

Item 13. The liquid crystal composition according to item 10, wherein the third component is a mixture of at least one compound selected from the group of compounds represented by formula (3-1) according to item 11 and at least one compound selected from the group of compounds represented by formula (3-7) according to item 11.

Item 14. The liquid crystal composition according to item 10, wherein the third component is a mixture of at least one compound selected from the group of compounds represented by formula (3-3) according to item 11 and at least one compound selected from the group of compounds represented by formula (3-7) according to item 11.

Item 15. The liquid crystal composition according to item 10, wherein the third component is a mixture of at least one compound selected from the group of compounds represented by formula (3-1) according to item 11, at least one compound selected from the group of compounds represented by formula (3-4) according to item 11 and at least one compound selected from the group of compounds represented by formula (3-13) according to item 11.

Item 16. The liquid crystal composition according to any one of items 10 to 15, wherein a ratio of the third component is in the range of 10% by weight to 80% by weight based on the total weight of the liquid crystal composition.

Item 17. The liquid crystal composition according to any one of items 1 to 16, further containing at least one compound selected from the group of compounds represented by formula (4) as a fourth component:

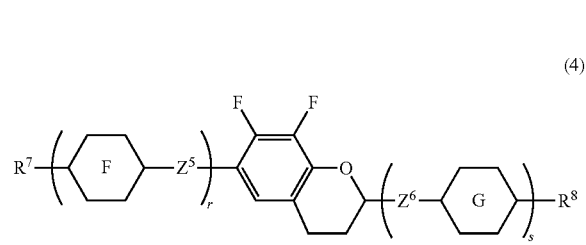
(4)

wherein $R^7$ and $R^8$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine; ring F and ring G are independently 1,4-cyclohexylene or 1,4-phenylene; $Z^5$ and $Z^6$ are independently a single bond, ethylene, methyleneoxy or carbonyloxy; r and s are independently 0, 1, 2 or 3, and a sum of r and s is 1, 2 or 3.

Item 18. The liquid crystal composition according to item 17, wherein the fourth component contains at least one compound selected from the group of compounds represented by formula (4-1) to formula (4-5):

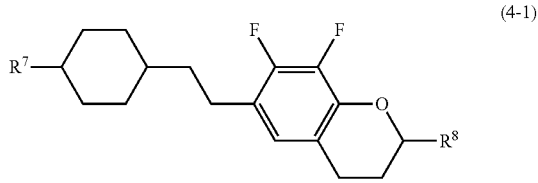
(4-1)

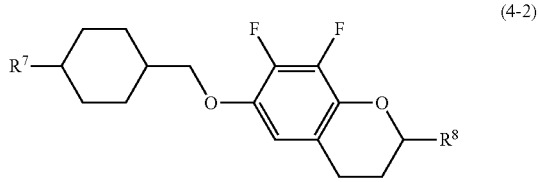
(4-2)

-continued

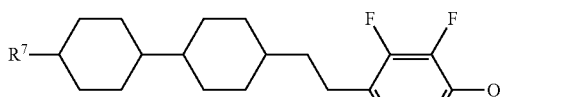

(4-3)

(4-4)

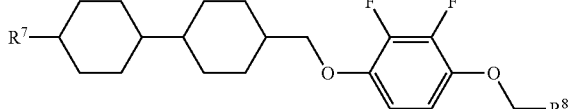

(4-5)

wherein $R^7$ and $R^8$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine.

Item 19. The liquid crystal composition according to item 17, wherein the fourth component is at least one compound selected from the group of compounds represented by formula (4-4) according to item 18.

Item 20. The liquid crystal composition according to any one of items 17 to 19, wherein a ratio of the fourth component is in the range of 5% by weight to 40% by weight based on the total weight of the liquid crystal composition.

Item 21. The liquid crystal composition according to any one of items 1 to 20, wherein a maximum temperature of a nematic phase is 70° C. or higher, an optical anisotropy (25° C.) at a wavelength of 589 nanometers is 0.08 or more, and a dielectric anisotropy (25° C.) at a frequency of 1 kHz is −2 or less.

Item 22. A compound represented by formula (1-1-1):

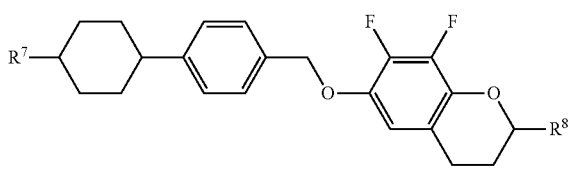

(1-1-1)

wherein p is an integer from 1 to 12; and $R^9$ is alkenyl having 2 to 12 carbons.

Item 23. A liquid crystal display device, containing the liquid crystal composition according to any one of items 1 to 21.

Item 24. The liquid crystal display device according to item 23, wherein an operating mode in the liquid crystal display device is a VA mode, an IPS mode, an FFS mode or a PSA mode, and a driving mode in the liquid crystal display device is an active matrix mode.

Item 25. Use of the liquid crystal composition according to any one of items 1 to 21 in the liquid crystal display device.

Item 26. A compound represented by formula (1-1-1) according to item 22: wherein p is an integer from 1 to 12; and $R^9$ is alkenyl having 2 to 3 carbons.

The invention further includes the following items: (1) the composition, further containing the optically active compound; (2) the composition, further containing the additive such as an antioxidant, an ultraviolet light absorber or an antifoaming agent; (3) an AM device containing the composition; (4) a device containing the composition, and having a TN, ECB, OCB, IPS, FFS, VA or PSA mode; (5) a transmissive device containing the composition; (6) use of the composition as the composition having the nematic phase; and (7) use as an optically active composition prepared by addition of the optically active compound to the composition.

The composition of the invention will be explained in the following order. First, a constitution of the component compounds in the composition will be explained. Second, main characteristics of the component compounds and main effects of the compounds on the composition will be explained. Third, a combination of components in the composition, a preferred ratio of the component compounds and the basis thereof will be explained. Fourth, a preferred embodiment of the component compounds will be explained. Fifth, specific examples of the component compounds will be shown. Sixth, the additive that may be mixed with the composition will be explained. Seventh, methods for synthesizing the component compounds will be explained. Last, an application of the composition will be explained.

First, the constitution of the component compounds in the composition will be explained. The composition of the invention is classified into composition A and composition B. Composition A may further contain any other liquid crystal compound, the additive and an impurity in addition to the liquid crystal compound selected from compound (1), compound (2), compound (3) and compound (4). "Any other liquid crystal compound" means a liquid crystal compound different from compound (1), compound (2), compound (3) and compound (4). Such a compound is mixed with the composition for the purpose of further adjusting the characteristics. Of any other liquid crystal compounds, a ratio of a cyano compound is preferably small in view of stability to heat or ultraviolet light. A further preferred ratio of the cyano compound is 0% by weight. The additive includes the optically active compound, the antioxidant, the ultraviolet light absorber, a coloring matter, the antifoaming agent, the polymerizable compound and a polymerization initiator. The impurity includes a compound mixed in a process such as preparation of the component compounds. Even in the case where the compound is liquid crystalline, the compound is classified as the impurity herein.

Composition B consists essentially of compounds selected from compound (1), compound (2), compound (3) and compound (4). A term "essentially" means that the composition does not contain any liquid crystal compound different from the compounds, except the additive and impurity. Composition B has a smaller number of components than composition A has. Composition B is preferred to composition A in view of cost reduction. Composition A is preferred to composition B in view of possibility of further adjusting physical properties by mixing any other liquid crystal compound.

Second, the main characteristics of the component compounds and the main effects of the compounds on the characteristics of the composition will be explained. The main characteristics of the component compounds are summarized in Table 2 on the basis of advantageous effects of the invention. In Table 2, a symbol L stands for "large" or "high," a symbol M stands for "medium," and a symbol S stands for "small" or "low." The symbols L, M and S represent a classification based on a qualitative comparison among the component compounds, and 0 (zero) means "a value is nearly zero."

TABLE 2

Characteristics of Compounds

| Compounds | Compound (1) | Compound (2) | Compound (3) | Compound (4) |
|---|---|---|---|---|
| Maximum Temperature | M | M to L | S to L | M to L |
| Viscosity | S | M to L | S to M | M to L |
| Optical Anisotropy | S | M to L | S to L | M to L |
| Dielectric Anisotropy | S | M to L | 0 | L |
| Specific Resistance | L | L | L | L |

Upon mixing the component compounds with the composition, the main effects of the component compounds on the characteristics of the composition are as described below. Compound (1) increases the absolute value of the dielectric anisotropy and decreases the minimum temperature. Compound (2) increases the absolute value of the dielectric anisotropy. Compound (3) increases the maximum temperature or decreases the minimum temperature and decreases the viscosity. Compound (4) increases the absolute value of the dielectric anisotropy and decreases the minimum temperature.

Third, the combination of the components in the composition, the preferred ratio of the component compounds and the basis thereof will be explained. The combination of the components in the composition includes a combination of the first component and the second component, a combination of the first component, the second component and the third component, a combination of the first component, the second component and the fourth component, and a combination of the first component, the second component, the third component and the fourth component. A preferred combination of the components in the composition includes the combination of the first component, the second component and the third component.

A preferred ratio of the first component is approximately 5% by weight or more for increasing the absolute value of the dielectric anisotropy, and approximately 80% by weight or less for decreasing the minimum temperature. A further preferred ratio is in the range of approximately 10% by weight to approximately 60% by weight. A particularly preferred ratio is in the range of approximately 20% by weight to approximately 40% by weight.

A preferred ratio of the second component is approximately 10% by weight or more for increasing the absolute value of the dielectric anisotropy, and approximately 95% by weight or less for decreasing the viscosity. A further preferred ratio is in the range of approximately 20% by weight to approximately 80% by weight. A particularly preferred ratio is in the range of approximately 30% by weight to approximately 60% by weight.

A preferred ratio of the third component is approximately 10% by weight or more for increasing the maximum temperature or decreasing the viscosity, and approximately 80% or less for decreasing the minimum temperature. A further preferred ratio is in the range of approximately 20% by weight to approximately 60% by weight. A particularly preferred ratio is in the range of approximately 30% by weight to approximately 50% by weight.

A preferred ratio of the fourth component is approximately 5% by weight or more for increasing the absolute value of the dielectric anisotropy, and approximately 40% by weight or less for decreasing the viscosity. A further preferred ratio is in the range of approximately 10% by weight to approximately 35% by weight. A particularly preferred ratio is in the range of approximately 15% by weight to approximately 30% by weight.

Fourth, the preferred embodiment of the component compounds will be explained.

$R^1$ is alkyl having 1 to 12 carbons in which a hydrogen atom is monosubstituted or disubstituted by a fluorine atom, $R^2$, $R^3$ and $R^4$ are independently alkyl having 1 to 12 carbons, alkoxy having 1 to 12 carbons or alkenyl having 2 to 12 carbons, or alkenyl having 2 to 12 carbons, $R^5$, $R^6$, $R^7$ and $R^8$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine, and $R^9$ is alkenyl having 2 to 12 carbons. Preferred $R^1$ is alkyl having 1 to 12 carbons in which terminal hydrogen is monosubstituted or disubstituted by fluorine for increasing the absolute value of the dielectric anisotropy, or alkyl having 1 to 3 carbons in which a hydrogen atom is monosubstituted or disubstituted by a fluorine atom for decreasing the viscosity. Preferred $R^2$, $R^3$, $R^5$, $R^6$ or $R^7$ is alkyl having 1 to 12 carbons for increasing the stability to ultraviolet light or heat, or alkenyl having 2 to 12 carbons for decreasing the viscosity. Preferred $R^4$ or $R^8$ is alkyl having 1 to 12 carbons for increasing the stability to ultraviolet light or heat, or alkoxy having 1 to 12 carbons for increasing the absolute value of the dielectric anisotropy. Preferred $R^9$ is alkenyl having 2 to 5 carbons for decreasing the viscosity.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in the alkenyl such as 1-propenyl, 1-butenyl, 1-pentenyl, 1-hexenyl, 3-pentenyl and 3-hexenyl for decreasing the viscosity, for instance. Cis preferred in the alkenyl such as 2-butenyl, 2-pentenyl and 2-hexenyl. In the alkenyl, straight-chain alkenyl is preferred to branched-chain alkenyl.

Preferred examples of the alkenyl in which at least one hydrogen is replaced by fluorine include 2,2-difluorovinyl, 3,3-difluoro-2-propenyl, 4,4-difluoro-3-butenyl, 5,5-difluoro-4-pentenyl and 6,6-difluoro-5-hexenyl. Further preferred examples include 2,2-difluorovinyl and 4,4-difluoro-3-butenyl for decreasing the viscosity.

Then, m and n are independently 0, 1, 2 or 3, and a sum of m and n is 1, 2 or 3. Preferred m or n is 1 for decreasing the minimum temperature and 2 for increasing the maximum temperature.

Then, p is an integer from 1 to 12. Preferred p is an integer from 1 to 3 for decreasing the viscosity. Moreover, q is 0, 1 or 2. Preferred q is 1 for decreasing the viscosity, and 2 for increasing the maximum temperature.

Then, r and s are independently 0, 1, 2 or 3, and a sum of r and s is 1, 2 or 3. Preferred r is 2 for increasing the maximum temperature. Preferred s is 0 for decreasing the minimum temperature.

Ring A and ring B are independently

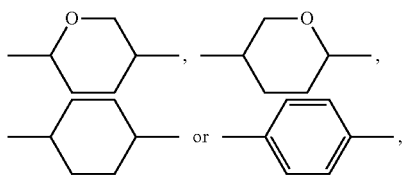

two of arbitrary ring A when m is 2 or 3 may be identical or different, and two of arbitrary ring B when n is 2 or 3 may be identical or different. Preferred ring A or ring B is 1,4-cyclohexylene for increasing the maximum temperature, 1,4-phenylene for increasing the optical anisotropy, and

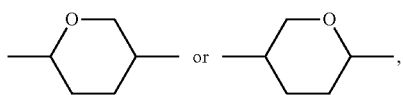

and is preferably

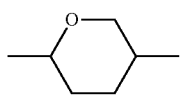

for increasing the absolute value of the dielectric anisotropy. Ring C, ring D and ring E are independently 1,4-cyclohexylene, 1,4-phenylene, 2-fluoro-1,4-phenylene or 3-fluoro-1,4-phenylene, and two of arbitrary ring C when q is 2 may be identical or different. Preferred ring C, ring D or ring E is 1,4-cyclohexylene for decreasing the viscosity, and 1,4-phenylene for increasing the optical anisotropy. Ring F and ring G are independently 1,4-cyclohexylene or 1,4-phenylene, two of arbitrary ring F when r is 2 or 3 may be identical or different, and two of arbitrary ring G when s is 2 or 3 may be identical or different. With regard to a configuration of 1,4-cyclohexylene, trans is preferred to cis for increasing the maximum temperature.

$X^1$ and $X^2$ are independently fluorine or chlorine. Preferred $X^1$ or $X^2$ is fluorine for decreasing the viscosity.

$Y^1$ is hydrogen or methyl. Preferred $Y^1$ is hydrogen for decreasing the viscosity.

$Z^1$ and $Z^2$ are independently a single bond, ethylene, methyleneoxy or carbonyloxy; two of arbitrary $Z^1$ when m is 2 or 3 may be identical or different, and two of arbitrary $Z^2$ when n is 2 or 3 may be identical or different. Preferred $Z^1$ or $Z^2$ is a single bond for decreasing the viscosity, and methyleneoxy for increasing the absolute value of the dielectric anisotropy. $Z^3$ and $Z^4$ are independently a single bond, ethylene, methyleneoxy or carbonyloxy, and two of arbitrary $Z^3$ when q is 2 may be identical or different. Preferred $Z^3$ is a single bond for decreasing the viscosity, and carbonyloxy for increasing the maximum temperature. $Z^5$ and $Z^6$ are independently a single bond, ethylene, methyleneoxy or carbonyloxy, two of arbitrary $Z^5$ when r is 2 or 3 may be identical or different, and two of arbitrary $Z^6$ when s is 2 or 3 may be identical or different. Preferred $Z^5$ or $Z^6$ is a single bond for decreasing the viscosity, and carbonyloxy for increasing the absolute value of the dielectric anisotropy.

Fifth, the specific examples of the component compounds will be shown. In the preferred compounds described below, $R^9$ is alkenyl having 1 to 12 carbons. $R^{10}$ and $R^{12}$ are independently straight-chain alkyl having 1 to 12 carbons or straight-chain alkenyl having 2 to 12 carbons. $R^{11}$ is straight-chain alkyl having 1 to 12 carbons or straight-chain alkoxy having 1 to 12 carbons. $R^{13}$ is straight-chain alkyl having 1 to 12 carbons, straight-chain alkoxy having 1 to 12 carbons or straight-chain alkenyl having 2 to 12 carbons.

Preferred compound (1) includes compound (1-1-1). Preferred compound (2) includes compound (2-1-1) to compound (2-12-1). Further preferred compound (2) includes compound (2-1-1) to compound (2-10-1). Particularly preferred compound (2) includes compound (2-1-1) to compound (2-7-1). Preferred compound (3) includes compound (3-1-1) to compound (3-13-1). Further preferred compound (3) includes compound (3-1-1) to compound (3-7-1), and compound (3-9-1) to compound (3-13-1). Particularly preferred compound (3) includes compound (3-1-1), compound (3-3-1), compound (3-4-1), compound (3-7-1) and compound (3-13-1). Preferred compound (4) includes compound (4-1-1) to compound (4-5-1). Further preferred compound (4) includes compound (4-4-1).

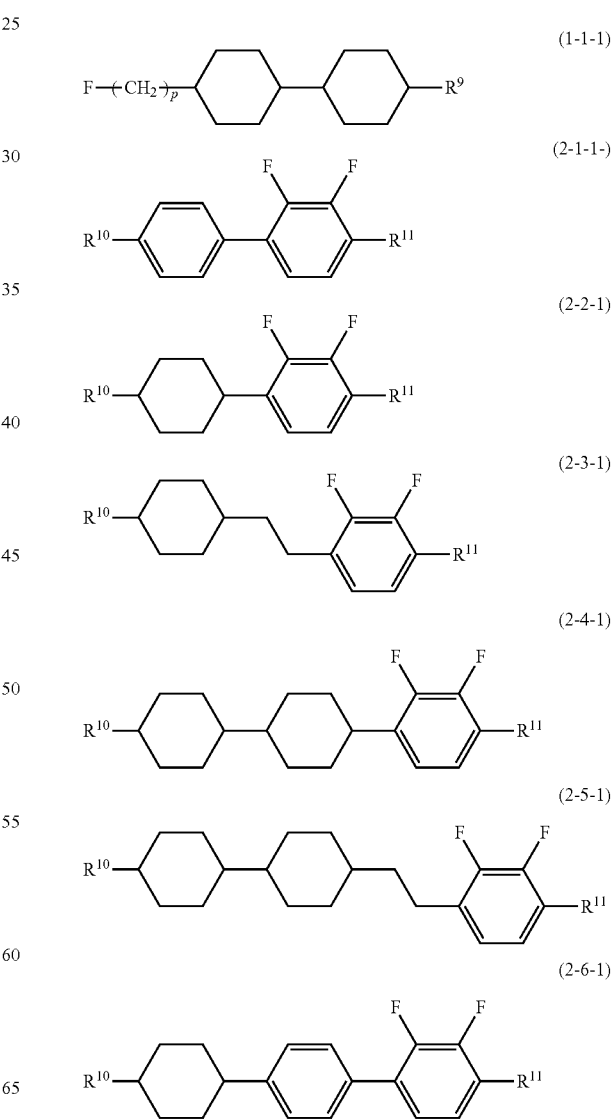

(2-7-1)
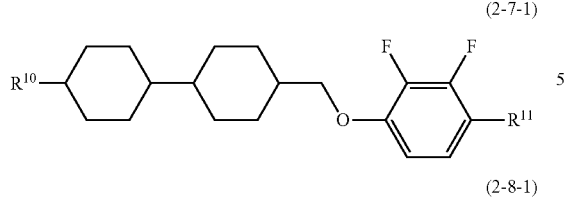
(2-8-1)
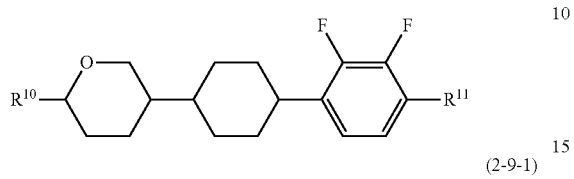
(2-9-1)
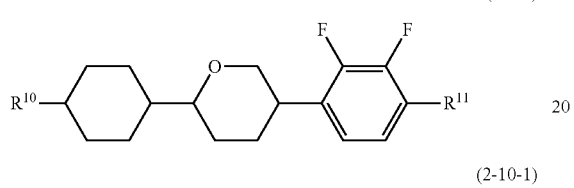
(2-10-1)
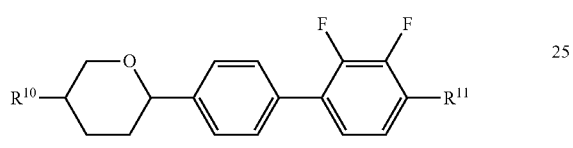
(2-11-1)
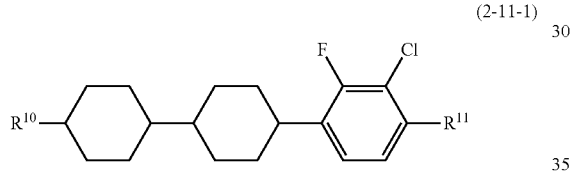
(2-12-1)
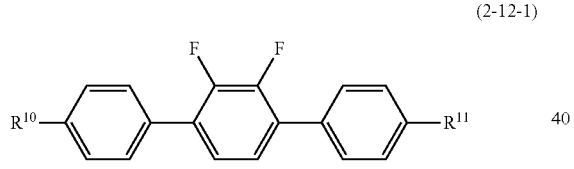
(3-1-1)
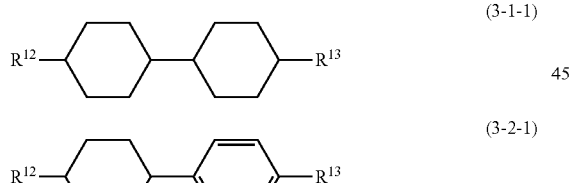
(3-2-1)
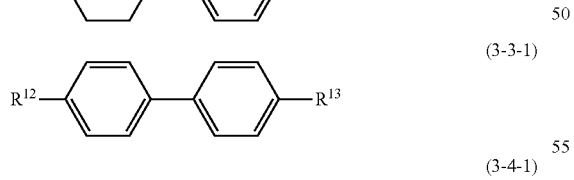
(3-3-1)
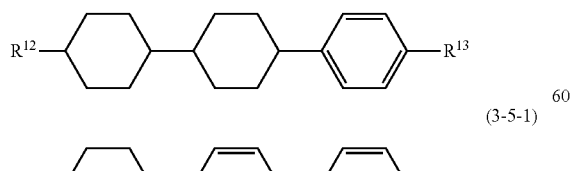
(3-4-1)
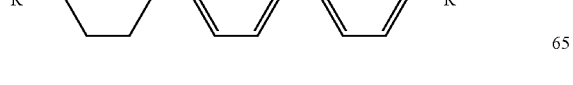
(3-5-1)
(3-6-1)
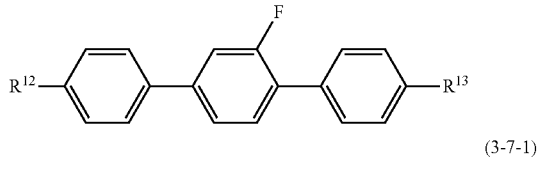
(3-7-1)
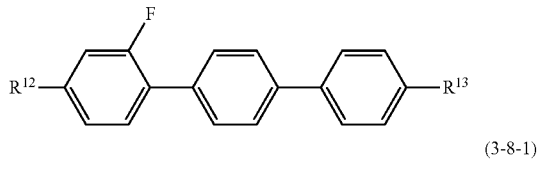
(3-8-1)
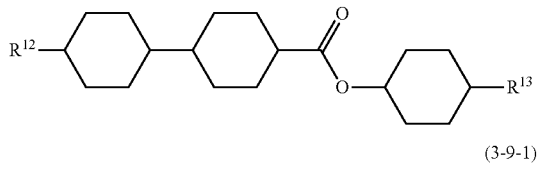
(3-9-1)
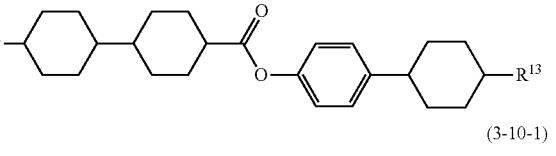
(3-10-1)
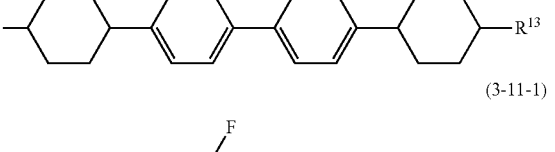
(3-11-1)
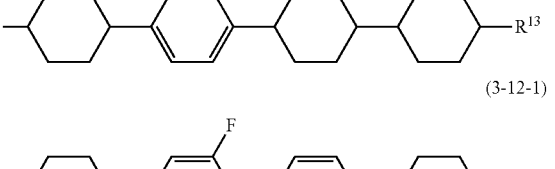
(3-12-1)
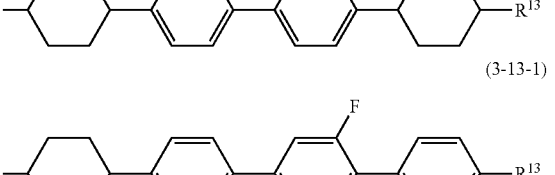
(3-13-1)
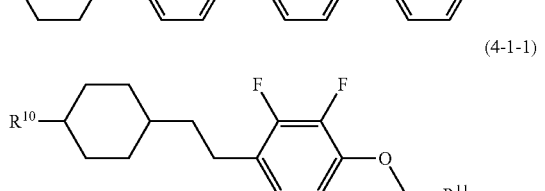
(4-1-1)
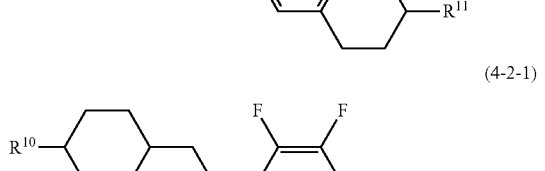
(4-2-1)
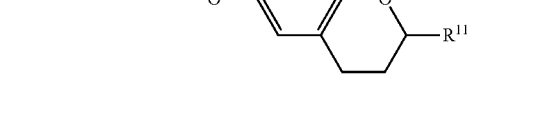

(4-3-1)
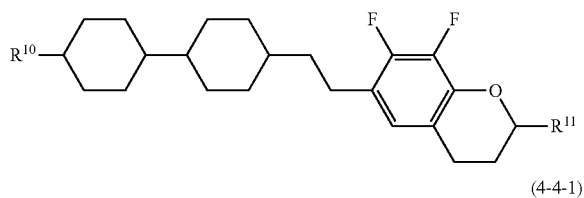

(4-4-1)
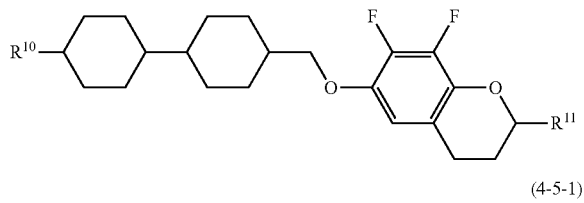

(4-5-1)
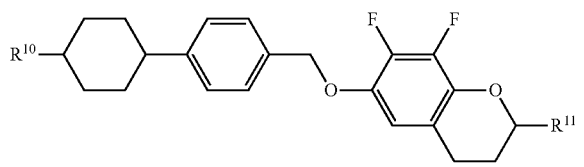

Sixth, the additive that may be mixed with the composition will be explained. Such an additive includes the optically active compound, the antioxidant, the ultraviolet light absorber, the coloring matter, the antifoaming agent, the polymerizable compound and the polymerization initiator. The optically active compound is mixed with the composition for the purpose of inducing a helical structure and giving a twist angle in the liquid crystals. Examples of such optically active compounds include compound (5-1) to compound (5-5). A preferred ratio of the optically active compound is approximately 5% by weight or less. A further preferred ratio is in the range of approximately 0.01% by weight to approximately 2% by weight.

(5-1)
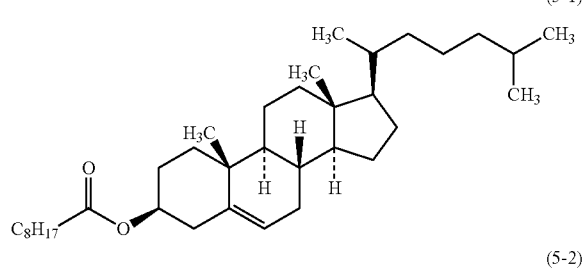

(5-2)
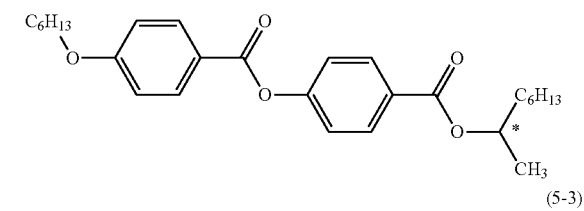

(5-3)
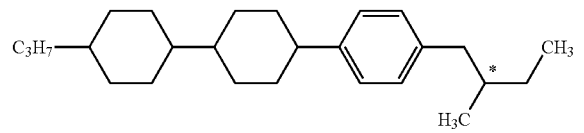

(5-4)
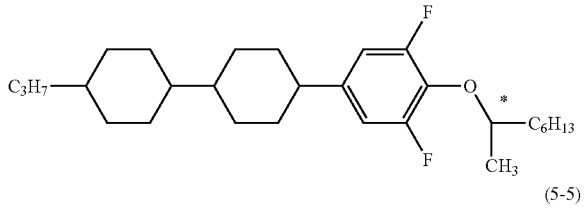

(5-5)
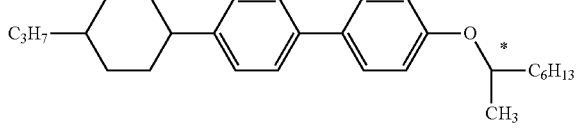

The antioxidant is mixed with the composition for the purpose of preventing a decrease in specific resistance caused by heating in air, or maintaining a large voltage holding ratio at room temperature and also at a temperature close to the maximum temperature of the nematic phase after the device has been used for a long period of time.

(6)
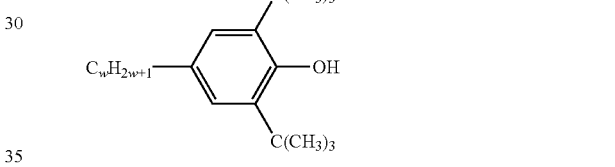

Preferred examples of the antioxidant include compound (6) where w is an integer from 1 to 9. In compound (6), preferred w is 1, 3, 5, 7 or 9. Further preferred w is 1 or 7. Compound (6) where w is 1 is effective in preventing a decrease in specific resistance caused by heating in air because the compound (6) has a large volatility. Compound (6) where w is 7 is effective in maintaining a large voltage holding ratio at room temperature and also at a temperature close to the maximum temperature of the nematic phase after the device has been used for a long period of time because the compound (6) has a small volatility. A preferred ratio of the antioxidant is approximately 50 ppm or more for achieving the effect thereof, and approximately 600 ppm or less for avoiding a decrease in maximum temperature or avoiding an increase in minimum temperature. A further preferred ratio is in the range of approximately 100 ppm to approximately 300 ppm.

Preferred examples of the ultraviolet light absorber include a benzophenone derivative, a benzoate derivative and a triazole derivative. A light stabilizer such as an amine having steric hindrance is also preferred. A preferred ratio of the ultraviolet light absorber or the stabilizer is approximately 50 ppm or more for achieving the effect thereof, and approximately 10,000 ppm or less for avoiding a decrease in maximum temperature or avoiding an increase in minimum temperature. A further preferred ratio is in the range of approximately 100 ppm to approximately 10,000 ppm.

A dichroic dye such as an azo dye or an anthraquinone dye is mixed with the composition to be adapted for a device having a guest host (GH) mode. A preferred ratio of the dye is in the range of approximately 0.01% by weight to approximately 10% by weight. The antifoaming agent such as dimethyl silicone oil or methyl phenyl silicone oil is mixed with the composition for preventing foam formation. A preferred ratio of the antifoaming agent is approximately 1 ppm or more for achieving the effect thereof, and approximately 1,000 ppm or less for avoiding a poor display. A further preferred ratio is in the range of approximately 1 ppm to approximately 500 ppm.

The polymerizable compound is mixed with the composition to be adapted for the device having the polymer sustained alignment (PSA) mode. Preferred examples of the polymerizable compound include a compound having a polymerizable group, such as acrylate, methacrylate, vinyl, vinyloxy, propenyl ether, epoxy (oxirane, oxetane) and vinyl ketone. Particularly preferred examples include an acrylate derivative or a methacrylate derivative. A preferred ratio of the polymerizable compound is approximately 0.05% by weight or more for achieving the effect thereof, and approximately 10% by weight or less for avoiding a poor display. A further preferred ratio is in the range of approximately 0.1% by weight to approximately 2% by weight. The polymerizable compound is preferably polymerized by irradiation with ultraviolet light or the like in the presence of a suitable initiator such as a photopolymerization initiator. Suitable conditions for polymerization, suitable types of the initiator and suitable amounts thereof are known to a person skilled in the art and are described in literatures. For example, Irgacure 651 (registered trademark), Irgacure 184 (registered trademark) or Darocure 1173 (registered trademark) (BASF), each being a photoinitiator, is suitable for radical polymerization. A preferred ratio of the photopolymerization initiator is in the range of approximately 0.1% by weight to approximately 5% by weight, and a particularly preferred ratio is in the range of approximately 1% by weight to approximately 3% by weight based on the polymerizable compound.

Seventh, the methods for synthesizing the component compounds will be explained. The compounds can be prepared according to known methods. Examples of the synthesizing methods are shown. Compound (1-1) is prepared by the method described in JP H11-035500 A (1999). Compound (2-2-1) and compound (2-3-1) are prepared by the method described in JP H2-503441 A (1990). Compound (2-9-1) is prepared by the method described in JP 2000-008040 A (2000). Compound (3-1-1) is prepared by the method described in JP S59-070624 A (1984). Compound (4-1-1) is prepared by the method described in JP 2005-035986 A (2005). The antioxidant is commercially available. A compound represented by formula (6) where w is 1 is available from Sigma-Aldrich Corporation. Compound (6) where w is 7 and so forth are prepared according to the method described in U.S. Pat. No. 3,660,505 B.

Any compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press), and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be explained. The composition of the invention mainly has a minimum temperature of approximately −10° C. or lower, a maximum temperature of approximately 70° C. or higher, and an optical anisotropy in the range of approximately 0.07 to approximately 0.20. The device containing the composition has a large voltage holding ratio. The composition is suitable for use in the AM device. The composition is particularly suitable for use in a transmissive AM device. The composition having an optical anisotropy in the range of approximately 0.08 to approximately 0.25, and also the composition having an optical anisotropy in the range of approximately 0.10 to approximately 0.30 may be prepared by adjusting the ratio of the component compounds or by mixing with any other liquid crystal compound. The composition can be used as the composition having the nematic phase and as the optically active composition by adding the optically active compound.

A preferred minimum temperature of the nematic phase of the liquid crystal composition of the invention is at least approximately 0° C. or lower, a further preferred minimum temperature of the nematic phase is approximately −20° C. or lower, and a particularly preferred minimum temperature of the nematic phase is approximately −30° C. or lower.

A preferred maximum temperature of the nematic phase of the liquid crystal composition of the invention is at least approximately 70° C. or higher, a further preferred maximum temperature of the nematic phase is approximately 75° C. or higher, and a particularly preferred maximum temperature of the nematic phase is approximately 80° C. or higher.

A preferred optical anisotropy at 25° C. and at a wavelength of 589 nanometers of the liquid crystal composition of the invention is in the range of approximately 0.07 to approximately 0.20, a further preferred optical anisotropy is in the range of approximately 0.07 to approximately 0.16, and a particularly preferred optical anisotropy is in the range of approximately 0.08 to approximately 0.12.

A preferred absolute value of the dielectric anisotropy at 25° C. of the liquid crystal composition of the invention is at least approximately 1.5 or more, a further preferred absolute value of the dielectric anisotropy is approximately 2 or higher, and a particularly preferred absolute value of the dielectric anisotropy is approximately 2.5 or higher.

The composition can be used for the AM device, and also for a PM device. The composition can be used for an AM device and a PM device having a mode such as PC, TN, STN, ECB, OCB, IPS, FFS, VA or PSA. Use for the AM device having the IPS, FFS or VA mode is particularly preferred. The device may be of a reflective type, a transmissive type or a transreflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network-polymer is formed in the composition.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

When a sample was a composition, the sample was measured as is, and values obtained were described. When the sample was a compound, a sample was prepared by mixing the compound (15% by weight) into mother liquid crystals (85% by weight). Values of characteristics of the compound were calculated from values obtained by measurement, according to an extrapolation method:
(extrapolated value)={(measured value of a sample)-0.85×(measured value of mother liquid crystals)}/0.15. When a smectic phase (or crystals) precipitated at the ratio thereof at 25° C., a ratio of the compound to the mother liquid crystals was changed step by step in the order of (10% by weight: 90% by weight), (5% by weight: 95% by weight) and (1% by weight: 99% by weight). Values of a maximum temperature, an optical anisotropy, viscosity and a dielectric anisotropy with regard to the compound were determined by the extrapolation method.

Components of the mother liquid crystals were as described below. The ratio of each component is expressed in terms of weight percent.

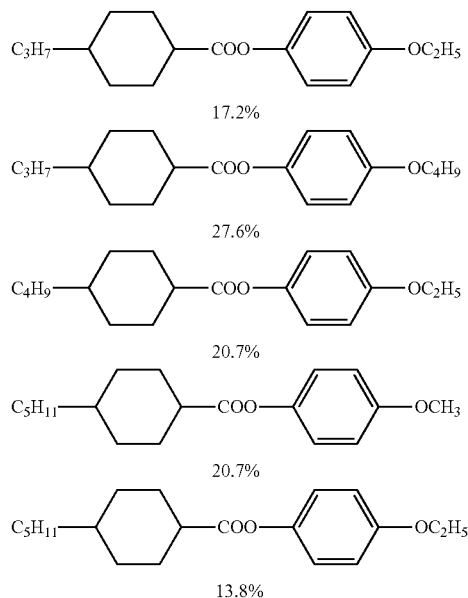

Characteristics were measured according to the methods described below. Most of the methods are applied as described in EIAJ ED-2521A of the Standard of Electronic Industries Association of Japan, or as modified thereon.

Maximum Temperature of a Nematic Phase (NI; ° C.):

A sample was placed on a hot plate in a melting point apparatus equipped with a polarizing microscope and was heated at a rate of 1° C. per minute. Temperature when a part of the sample began to change from a nematic phase to an isotropic liquid was measured. A higher limit of a temperature range of the nematic phase may be abbreviated as "maximum temperature."

Minimum Temperature of a Nematic Phase ($T_c$; ° C.):

A sample having a nematic phase was put in glass vials and kept in freezers at 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as "≤−20° C." A lower limit of a temperature range of the nematic phase may be abbreviated as "minimum temperature."

Viscosity (Bulk Viscosity; η; Measured at 20° C.; mPa·s):

A cone-plate (E type) viscometer was used for measurement.

Optical Anisotropy (Refractive Index Anisotropy; Δn; Measured at 25° C.):

Measurement was carried out by means of an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

Dielectric Anisotropy (Δ∈; Measured at 25° C.):

A value of dielectric anisotropy was calculated from an equation: Δ∈=∈∥−∈⊥. A dielectric constant (∈⊥ and ∈⊥) was measured as described below.

1) Measurement of Dielectric Constant (∈∥):

An ethanol (20 mL) solution of octadecyl triethoxysilane (0.16 mL) was applied to a well-washed glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (Eli) in the major axis direction of liquid crystal molecules was measured.

2) Measurement of Dielectric Constant (∈⊥):

A polyimide solution was applied to a well-washed glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

Threshold Voltage (Vth; Measured at 25° C.; V):

An LCD-5100 luminance meter made by Otsuka Electronics Co., Ltd. was used for measurement. A light source was a halogen lamp. A sample was put in a VA device having a normally black mode, in which a distance (cell gap) between two glass substrates was 4 micrometers and a rubbing direction was anti-parallel, and the device was sealed with an ultraviolet-curable adhesive. Voltage (60 Hz, rectangular waves) to be applied to the device was stepwise increased from 0 V to 20 V at an increment of 0.02 V. On the occasion, the device was irradiated with light from a direction perpendicular to the device, and the amount of light passing through the device was measured. A voltage-transmittance curve was prepared, in which the maximum amount of light corresponds to 100% transmittance and the minimum amount of light corresponds to 0% transmittance. A threshold voltage is voltage at 10% transmittance.

Voltage Holding Ratio (VHR-1; Measured at 25° C.; %):

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is a percentage of area A to area B.

Voltage Holding Ratio (VHR-2; Measured at 80° C.; %):

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is a percentage of area A to area B.

Voltage Holding Ratio (VHR-3; Measured at 25° C.; %):

Stability to ultraviolet light was evaluated by measuring a voltage holding ratio after irradiation with ultraviolet light. A TN device used for measurement had a polyimide alignment film and a cell gap was 5 micrometers. A sample was injected into the device, and then the device was irradiated with light for 20 minutes. A light source was an ultra high-pressure mercury lamp USH-500D (made by Ushio, Inc.), and a distance between the device and the light source was 20 centimeters. In measuring VHR-3, a decaying voltage was measured for 16.7 milliseconds. A composition having a large VHR-3 has a high stability to ultraviolet light. A value of VHR-3 is preferably in the range of 90% or more, further preferably, 95% or more.

Voltage Holding Ratio (VHR-4; Measured at 25° C.; %):

A TN device into which a sample was injected was heated in a constant-temperature bath at 80° C. for 500 hours, and then stability to heat was evaluated by measuring a voltage holding ratio. In measuring VHR-4, a decaying voltage was measured for 16.7 milliseconds. A composition having a large VHR-4 has a high stability to heat.

Response Time (τ; Measured at 25° C.; Millisecond):

An LCD-5100 luminance meter made by Otsuka Electronics Co., Ltd. was used for measurement. A light source was a halogen lamp. A low-pass filter was set at 5 kHz. A sample was put in a VA device having a normally black mode, in which a distance (cell gap) between two glass substrates was 3.2 micrometers and a rubbing direction was anti-parallel, and the device was sealed with an ultraviolet-curable adhesive. Voltage a little over a threshold voltage was applied to the device for approximately one minute, next, the device was irradiated with ultraviolet light at 23.5 mW/cm$^2$ for approximately 8 minutes while applying a voltage of 5.6 V. Rectangular waves (60 Hz, 10 V, 0.5 second) were applied to the device. On the occasion, the device was irradiated with light from a direction perpendicular to the device, and the amount of light passing through the device was measured. The maximum amount of light corresponds to 100% transmittance, and the minimum amount of light corresponds to 0% transmittance. A response time is a period of time required for a change from 90% transmittance to 10% transmittance (fall time; millisecond).

Specific Resistance (ρ; Measured at 25° C.; Ωcm):

Into a vessel equipped with an electrode, 1.0 milliliter of a sample was injected. A DC voltage (10 V) was applied to the vessel, and a DC current after 10 seconds was measured. A specific resistance was calculated from the following equation:

$$\text{(specific resistance)} = \{\text{(voltage)} \times \text{(electric capacity of vessel)}\} / \{\text{(DC current)} \times \text{(dielectric constant of vacuum)}\}.$$

$^1$H-NMR Analysis:

As a measuring apparatus, DRX-500 (made by Bruker BioSpin Corporation) was used. A sample prepared in Example and so forth was dissolved in a deuterated solvent such as CDCl$_3$ in which the sample was soluble, and measurement was carried out under the conditions of room temperature, 500 MHz and 24 times of accumulation. In addition, in explaining magnetic resonance spectra obtained, s, d, t, q and m mean a singlet, a doublet, a triplet, a quartet and a multiplet, respectively. Moreover, tetramethylsilane (TMS) was used as a reference material for a zero point of chemical shifts (δ values). $^{19}$F-NMR analysis was also carried out by means of the identical measuring apparatus.

Gas Chromatographic Analysis:

GC-14B gas chromatograph made by Shimadzu Corporation was used for measurement. A carrier gas was helium (2 mL per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting a sample, chloroform, hexane and so forth may also be used. The following capillary columns may also be used for separating the component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A ratio of liquid crystal compounds included in a composition may be calculated according to the method as described below. The liquid crystal compounds can be detected by means of a gas chromatograph. A ratio of peak areas in a gas chromatogram corresponds to a ratio (in the number of moles) of the liquid crystal compounds. When the capillary columns described above were used, a correction coefficient of each of the liquid crystal compounds may be regarded as 1 (one). Accordingly, a ratio (% by weight) of the liquid crystal compounds was calculated from the ratio of the peak areas.

The invention will be explained in detail by way of Examples. The invention is not limited by the Examples described below. The compounds described in Comparative Examples and Examples were expressed using symbols according to definitions in Table 3 below. In Table 3, a configuration of 1,4-cyclohexylene is trans. A parenthesized number next to a symbolized compound in Examples corresponds to the number of the compound. A symbol (–) means any other liquid crystal compound. A ratio (percentage) of liquid crystal compounds means weight percent (% by weight) based on the total weight of the liquid crystal composition. The liquid crystal composition includes an impurity. Last, values of characteristics of the composition were summarized.

TABLE 3

Method for Description of Compounds using Symbols
R—(A₁)—Z₁—...—Zₙ—(Aₙ)—R'

1) Left-terminal Group / R-Symbol

| | |
|---|---|
| $C_nH_{2n+1}$— | n- |
| $C_nH_{2n+1}O$— | nO— |
| $C_mH_{2m+1}OC_nH_{2n}$— | mOn- |
| $CH_2=CH$— | V— |
| $C_nH_{2n+1}$—CH=CH— | nV— |
| $CH_2=CH$—$C_nH_{2n}$— | Vn- |
| $C_mH_{2m+1}$—CH=CH—$C_nH_{2n}$— | mVn- |
| $CF_2=CH$— | VFF— |
| $CF_2=CH$—$C_nH_{2n}$— | VFFn- |
| F—$C_nH_{2n}$— | Fn- |
| $C_nH_{2n+1}$—$CF_2$— | nCF2— |

2) Right-terminal Group / -Symbol

| | |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —CH=$CF_2$ | —VFF |

3) Bonding Group —$Z_n$— / Symbol

| | |
|---|---|
| —$C_nH_{2n}$— | n |
| —COO— | E |
| —CH=CH— | V |
| —$CH_2O$— | 1O |
| —$OCH_2$— | O1 |
| —$SiH_2$— | Si |

4) Ring Structure —$A_n$— / Symbol

 H

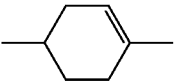 Ch

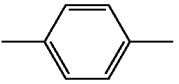 B

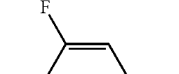 B(2F)

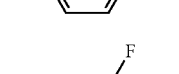 B(F)

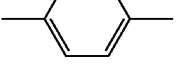 B(F, F)

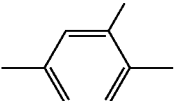 B(2F, 3F)

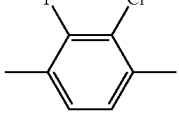 B(2F, 3CL)

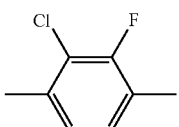 B(2CL, 3F)

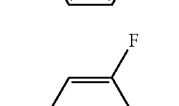 B(3F, 6F)

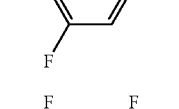 B(2F, 3F, 6Me)

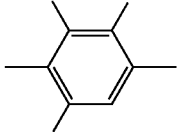 dh

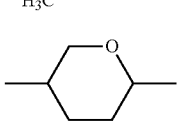 Dh

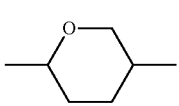 Cro(7F, 8F)

5) Examples of Description

Example 1

F3-HH-V

Example 2

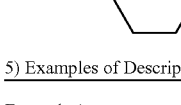

3CF2-HH-3

Example 3

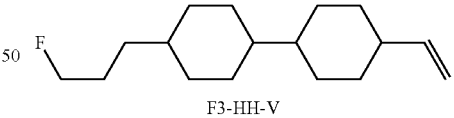

5-HBB(F)B-3

TABLE 3-continued

Method for Description of Compounds using Symbols
R—(A₁)—Z₁—...—Zₙ—(Aₙ)—R'

Example 4

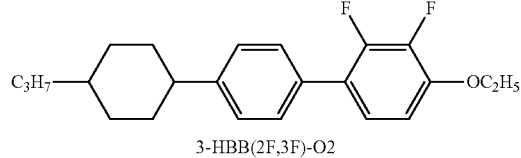

3-HBB(2F,3F)-O2

Example 1

Among types of compound (1-1-1), the following compound was prepared.

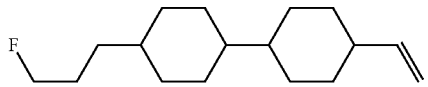

$^1$H-NMR (CDCl$_3$; δ ppm): 5.77 (ddd, 1H, J=17 Hz, 10.5 Hz, 6.5 Hz), 4.95 (ddd, 1H, J=17 Hz, 1.5 Hz, 1.5 Hz), 4.87 (ddd, 1H, J=11 Hz, 1.5 Hz, 1.5 Hz), 4.42 (dt, 2H, J=47.5 Hz, 6.2 Hz), 1.92-1.82 (m, 1H), 1.78-1.64 (m, 10H), 1.28-1.24 (m, 2H), 1.21-1.12 (m, 1H), 1.10-0.84 (m, 10H); $^{19}$F-NMR (CDCl$_3$; δ ppm): −218.0 (tt, 1F, J=95.0 Hz, 23.8 Hz).

Phase transition temperature was Cr 3.0 SB 36.0 N 53.4 Iso. Herein, Cr, SB, N and Iso stand for a crystal, a smectic B phase, a nematic phase and an isotropic liquid, respectively, and all of units of the phase transition temperature were ° C. Moreover, the compound was mixed with mother liquid crystals and values of characteristics of the compound were determined by an extrapolation method. NI=33.9° C.; Δ∈=−1.0; Δn=0.039.

Example 2

Among types of compound (1-1-1), the following compound was prepared.

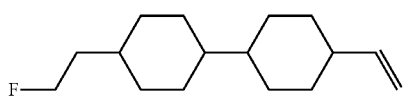

$^1$H-NMR (CDCl$_3$; δ ppm): 5.77 (ddd, 1H, J=17 Hz, 10.5 Hz, 6.5 Hz), 4.95 (ddd, 1H, J=17 Hz, 1.5 Hz, 1.5 Hz), 4.87 (ddd, 1H, J=10.5 Hz, 1.5 Hz, 1.5 Hz), 4.49 (dt, 2H, J=47.5 Hz, 6.2 Hz), 1.92-1.83 (m, 1H), 1.80-1.71 (m, 8H), 1.58 (ddt, 2H, J=26 Hz, 6.5 Hz, 6.2 Hz), 1.41-1.33 (m, 1H), 1.10-0.89 (m, 10H); $^{19}$F-NMR (CDCl$_3$; δ ppm): −218.3 (tt, 1F, J=47.5 Hz, 52.9 Hz).

Phase transition temperature was Cr −26.2 SB 41.4 Iso. Herein, Cr, SB and Iso stand for a crystal, a smectic B phase and an isotropic liquid, respectively, and all of units of the phase transition temperature were ° C. Moreover, the compound was mixed with mother liquid crystals and values of characteristics of the compound were determined by an extrapolation method. NI=15.0° C.; Δ∈=−0.6; Δn=0.024.

Example 3

Among types of compound (1-1-1), the following compound was prepared.

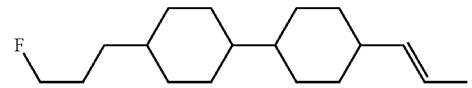

$^1$H-NMR (CDCl$_3$; δ ppm): 5.41-5.33 (m, 2H), 4.42 (dt, 2H, J=47.4 Hz, J=6.3 Hz), 1.80-1.66 (m, 11H), 1.63 (d, 3H, J=4.1 Hz), 1.28-1.23 (m, 2H), 1.20-1.11 (m, 1H), 1.06-0.83 (m, 10H). $^{19}$F-NMR (CDCl$_3$; δ ppm) −218.05 (dt, 1F, J=47.4 Hz, J=24.4 Hz).

Phase transition temperature was Cr 43.6 SB 49.8 N 87.2 Iso. Herein, Cr, SB, N and Iso stand for a crystal, a smectic B phase, nematic phase and an isotropic liquid, respectively, and all of units of the phase transition temperature were ° C. Moreover, the compound was mixed with mother liquid crystals and values of characteristics of the compound were determined by an extrapolation method. NI=77.0° C.; Δ∈=−2.6; Δn=0.064.

Example 4

Among types of compound (1-1-1), the following compound was prepared.

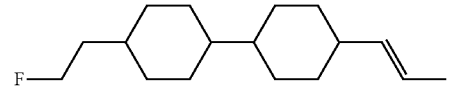

$^1$H-NMR (CDCl$_3$; δ ppm) 5.41-5.33 (m, 2H), 4.49 (dt, 2H, J=47.4 Hz, J=6.3 Hz), 1.80-1.71 (m, 8H), 1.63 (d, 3H, J=4.9 Hz), 1.62-1.51 (m, 2H), 1.41-1.25 (m, 2H), 1.06-0.87 (m, 10H). $^{19}$F-NMR (CDCl$_3$; δ ppm) −218.35 (dt, 1F, J=47.4 Hz, J=24.4 Hz).

Phase transition temperature was Cr 1.4 SB 40.4 Iso. Herein, Cr, SB and Iso stand for a crystal, a smectic B phase and an isotropic liquid, respectively, and all of units of the phase transition temperature were ° C. Moreover, the compound was mixed with mother liquid crystals and values of characteristics of the compound were determined by an extrapolation method. NI=44.7° C.; Δ∈=−0.9; Δn=0.049.

Example 5

Among types of compound (1-1-1), the following compound was prepared.

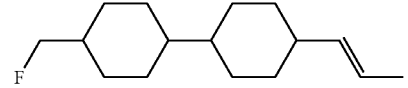

$^1$H-NMR (CDCl$_3$; δ ppm) 5.43-5.35 (m, 2H), 4.24 (dd, 2H, J=47.7 Hz, J=6.1 Hz), 1.83-1.57 (m, 11H), 1.66 (d, 3H, J=4.5 Hz), 1.10-0.97 (m, 10H), $^{19}$F-NMR (CDCl$_3$; δ ppm)-222.82 (dt, 1F, J=47.7 Hz, J=16.7 Hz).

Phase transition temperature was Cr 14.0 N 22.1 Iso. Herein, Cr, N and Iso stand for a crystal, nematic phase and an isotropic liquid, respectively, and all of units of the phase transition temperature were ° C. Moreover, the compound was mixed with mother liquid crystals and values of characteristics of the compound were determined by an extrapolation method. NI=19.7° C.; Δ∈=−0.8; Δn=0.037.

Comparative Example 1

From the compositions disclosed in JP H11-035500 A, Example 1 was selected. The basis of selection is that the composition contains compound (1). Components and characteristics of the composition were as described below. According to Comparative Example 1, the composition had a positive dielectric anisotropy (Δ∈), and resulted in no satisfactory solution to problem of the invention. Moreover, other examples of compositions disclosed in JP H11-035500 A also resulted in no satisfactory solution of problem of the invention in a similar manner.

| | | |
|---|---|---|
| 3CF2-HH-3 | (1) | 10% |
| 4CF2-HH-3 | (1) | 10% |
| 7-HB(F,F)-F | (—) | 5% |
| 2-HHB(F)-F | (—) | 7% |
| 3-HHB(F)-F | (—) | 7% |
| 5-HHB(F,F)-F | (—) | 7% |
| 3-H2HB(F,F)-F | (—) | 9% |
| 5-H2HB(F,F)-F | (—) | 5% |
| 3-HH2B(F,F)-F | (—) | 8% |
| 5-HH2B(F,F)-F | (—) | 7% |
| 3-HHB(F,F)-F | (—) | 8% |
| 5-HHB(F,F)-F | (—) | 7% |
| 3-HHB-F | (—) | 5% |
| 3-HBB-F | (—) | 5% |

NI=80.8° C.; Δn=0.0689; η=24.9 mPa·s; Δ∈=4.7.

Comparative Example 2

A liquid crystal composition containing a compound similar to compound (1) was prepared, and measurement was carried out according to the method described above. Components and characteristics of the composition were as described below. The minimum temperature of the liquid crystal composition was in the range of −10° C. to −20° C.

| | | |
|---|---|---|
| 3-HH-VFF | Similar to (1) | 29% |
| 3-HB(2F,3F)-O2 | (2-2-1) | 10% |
| V-HB(2F,3F)-O2 | (2-2-1) | 12% |
| 3-HBB(2F,3F)-O2 | (2-6-1) | 10% |
| 5-HBB(2F,3F)-O2 | (2-6-1) | 3% |
| 3-HH1OB(2F,3F)-O2 | (2-7-1) | 11% |
| 3-HH-4 | (3-1-1) | 11% |
| 5-B(F)BB-2 | (3-7-1) | 14% |

NI=70.8° C.; Tc<−10° C.; Δn=0.102; η=16.0 mPa·s; Δ∈=−2.3; VHR-1=99.1%; VHR-2=96.3%; VHR-3=95.5%.

Example 6

The compound similar to compound (1) in Comparative Example 2 was replaced by compound (1-1-1). The composition was prepared and measurement was carried out according to the method described above. Components and characteristics of the composition were as described below. According to Example 6, the composition had a lower minimum temperature and a larger negative dielectric anisotropy in comparison with the composition according to Comparative Example 1.

| | | |
|---|---|---|
| F3-HH-V | (1-1-1) | 29% |
| 3-HB(2F,3F)-O2 | (2-2-1) | 10% |
| V-HB(2F,3F)-O2 | (2-2-1) | 12% |
| 3-HBB(2F,3F)-O2 | (2-6-1) | 10% |
| 5-HBB(2F,3F)-O2 | (2-6-1) | 3% |
| 3-HH1OB(2F,3F)-O2 | (2-7-1) | 11% |
| 3-HH-4 | (3-1-1) | 11% |
| 5-B(F)BB-2 | (3-7-1) | 14% |

NI=69.8° C.; Tc<−30° C.; Δn=0.101; η=16.7 mPa·s; Δ∈=−3.1; VHR-1=99.2%; VHR-2=97.8%; VHR-3=96.6%.

Example 7

| | | |
|---|---|---|
| F3-HH-V | (1-1-1) | 20% |
| 3-BB(2F,3F)-O2 | (2-1-1) | 5% |
| 5-HB(2F,3F)-O2 | (2-2-1) | 5% |
| 3-H2B(2F,3F)-O2 | (2-3-1) | 11% |
| 2-HHB(2F,3F)-O2 | (2-4-1) | 3% |
| 3-HHB(2F,3F)-O2 | (2-4-1) | 5% |
| 4-HHB(2F,3F)-O2 | (2-4-1) | 5% |
| V2-HHB(2F,3F)-O2 | (2-4-1) | 3% |
| 3-HH1OB(2F,3F)-O2 | (2-7-1) | 5% |
| 5-HH1OB(2F,3F)-O2 | (2-7-1) | 5% |
| 2-HH-3 | (3-1-1) | 12% |
| 3-HH-4 | (3-1-1) | 11% |
| 5-B(F)BB-2 | (3-7-1) | 10% |

NI=71.1° C.; Tc<−30° C.; Δn=0.087; η=16.4 mPa·s; Δ∈=−3.3; VHR-1=99.1%; VHR-2=97.9%; VHR-3=96.8%.

Example 8

| | | |
|---|---|---|
| F3-HH-V | (1-1-1) | 20% |
| 5-BB(2F,3F)-O2 | (2-1-1) | 5% |
| 5-H2B(2F,3F)-O2 | (2-3-1) | 7% |
| 2-HHB(2F,3F)-1 | (2-4-1) | 8% |
| 3-HHB(2F,3F)-1 | (2-4-1) | 8% |
| 3-HH2B(2F,3F)-O2 | (2-5-1) | 8% |
| 5-HBB(2F,3F)-O2 | (2-6-1) | 3% |
| 3-DhHB(2F,3F)-O2 | (2-8-1) | 4% |
| 3-HDhB(2F,3F)-O2 | (2-9-1) | 4% |
| 3-dhBB(2F,3F)-O2 | (2-10-1) | 3% |
| 3-HH-4 | (3-1-1) | 10% |
| 3-HH-V | (3-1-1) | 10% |
| 3-HB-O2 | (3-2-1) | 10% |

NI=72.1° C.; Tc≤−30° C.; Δn=0.080; η=15.9 mPa·s; Δ∈=−3.2; VHR-1=99.0%; VHR-2=97.7%; VHR-3=96.5%.

Example 9

| | | |
|---|---|---|
| F2-HH-V | (1-1-1) | 8% |
| F3-HH-V | (1-1-1) | 18% |
| F3-HH-2V1 | (1-1-1) | 10% |
| 3CF2-HH-3 | (1) | 3% |
| 3-H2B(2F,3F)-O4 | (2-3-1) | 18% |
| 2-HHB(2F,3F)-1 | (2-4-1) | 6% |
| 3-HHB(2F,3F)-1 | (2-4-1) | 7% |
| 3-HH2B(2F,3F)-O2 | (2-5-1) | 7% |
| 5-HH2B(2F,3F)-O2 | (2-5-1) | 8% |
| 3-HH1OB(2F,3F)-1 | (2-7-1) | 5% |
| 2-BB(2F,3F)B-3 | (2-12-1) | 3% |
| 2-BB(2F,3F)B-4 | (2-12-1) | 7% |

NI=70.1° C.; Tc≤−30° C.; Δn=0.087; η=17.1 mPa·s; Δ∈=−3.1; VHR-1=99.1%; VHR-2=97.5%; VHR-3=96.8%.

Example 10

| F3-HH-V | (1-1-1) | 20% |
|---|---|---|
| 5-HB(2F,3F)-O2 | (2-2-1) | 7% |
| 1V2-HB(2F,3F)-O2 | (2-2-1) | 3% |
| 3-H2B(2F,3F)-O4 | (2-3-1) | 12% |
| 5-HH2B(2F,3F)-O2 | (2-5-1) | 5% |
| V2-HBB(2F,3F)-O2 | (2-6-1) | 3% |
| 3-HH1OB(2F,3F)-O2 | (2-7-1) | 5% |
| 5-HH1OB(2F,3F)-O2 | (2-7-1) | 5% |
| 5-HDhB(2F,3F)-O2 | (2-9-1) | 4% |
| 3-HHB(2F,3CL)-O2 | (2-11-1) | 3% |
| 2-BB(2F,3F)B-4 | (2-12-1) | 5% |
| 3-HH-V | (3-1-1) | 5% |
| 5-HH-V | (3-1-1) | 5% |
| 3-HH-V1 | (3-1-1) | 5% |
| 1-BB-3 | (3-3-1) | 5% |
| V2-BB-1 | (3-3-1) | 3% |
| 2-BB(F)B-5 | (3-6-1) | 2% |
| 5-HBB(F)B-2 | (3-13-1) | 3% |

NI=70.8° C.; Tc≤30° C.; Δn=0.098; η=16.6 mPa·s; Δ∈=−3.3; VHR-1=99.2%; VHR-2=97.4%; VHR-3=96.6%.

Example 11

| F3-HH-V | (1-1-1) | 12% |
|---|---|---|
| 4CF2-HH-3 | (1) | 8% |
| 5-H2B(2F,3F)-O2 | (2-3-1) | 10% |
| 5-HH2B(2F,3F)-O2 | (2-5-1) | 8% |
| 3-HH1OB(2F,3F)-O2 | (2-7-1) | 4% |
| 5-HH1OB(2F,3F)-O2 | (2-7-1) | 8% |
| 2-HDhB(2F,3F)-O2 | (2-9-1) | 3% |
| 3-HH-O1 | (3-1-1) | 3% |
| 3-HH-V | (3-1-1) | 8% |
| 1-HH-2V1 | (3-1-1) | 5% |
| 3-HH-2V1 | (3-1-1) | 3% |
| 3-HB-O1 | (3-2-1) | 3% |
| 1-BB-5 | (3-3-1) | 7% |
| 1V2-BB-1 | (3-3-1) | 3% |
| 3-HHB-O1 | (3-4-1) | 3% |
| 3-HBB-2 | (3-5-1) | 3% |
| 3-H2Cro(7F,8F)-5 | (4-1-1) | 3% |
| 3-HH2Cro(7F,8F)-5 | (4-3-1) | 3% |
| 5-HB1OCro(7F,8F)-5 | (4-5-1) | 3% |

NI=70.8° C.; Tc<−30° C.; Δn=0.085; η=19.2 mPa·s; Δ∈=−3.4; VHR-1=98.9%; VHR-2=97.1%; VHR-3=96.2%.

Example 12

| F3-HH-V | (1-1-1) | 16% |
|---|---|---|
| 3V-HB(2F,3F)-O2 | (2-2-1) | 3% |
| 3-H2B(2F,3F)-O2 | (2-3-1) | 10% |
| 3-H2B(2F,3F)-O4 | (2-3-1) | 12% |
| 3-HH2B(2F,3F)-O2 | (2-5-1) | 8% |
| 5-HH2B(2F,3F)-O2 | (2-5-1) | 9% |
| 3-HHB(2CL,3F)-O2 | (2) | 2% |
| 3-HH-V | (3-1-1) | 12% |
| 3-HH-V1 | (3-1-1) | 3% |
| V2-BB-1 | (3-3-1) | 3% |
| V2-BB(F)B-3 | (3-6-1) | 3% |
| 5-B(F)BB-2 | (3-7-1) | 3% |
| 3-HHEH-5 | (3-8-1) | 3% |
| 3-HHEBH-3 | (3-9-1) | 3% |
| 5-H1OCro(7F,8F)-5 | (4-2-1) | 3% |
| 3-HH1OCro(7F,8F)-5 | (4-4-1) | 4% |
| 4O-Cro(7F,8F)H-3 | (4) | 3% |

NI=71.1° C.; Tc<−30° C.; Δn=0.086; η=19.8 mPa·s; Δ∈=−3.4; VHR-1=98.8%; VHR-2=96.9%; VHR-3=96.2%.

Example 13

| F3-HH-V | (1-1-1) | 15% |
|---|---|---|
| 3-H2B(2F,3F)-O2 | (2-3-1) | 10% |
| 3-H2B(2F,3F)-O4 | (2-3-1) | 7% |
| 5-H2B(2F,3F)-O2 | (2-3-1) | 10% |
| 1V2-HHB(2F,3F)-O2 | (2-4-1) | 2% |
| 3-HH2B(2F,3F)-O2 | (2-5-1) | 5% |
| 3-HH1OB(2F,3F)-1 | (2-7-1) | 3% |
| 3-DhHB(2F,3F)-O2 | (2-8-1) | 3% |
| 3-HDhB(2F,3F)-O2 | (2-9-1) | 5% |
| 3-HH-V | (3-1-1) | 13% |
| 5-HB-3 | (3-2-1) | 7% |
| 1-BB-3 | (3-3-1) | 5% |
| 5-B(F)BB-3 | (3-7-1) | 3% |
| 3-HBBH-3 | (3-10-1) | 3% |
| 3-HB(F)HH-5 | (3-11-1) | 3% |
| 5-HB(F)BH-5 | (3-12-1) | 3% |
| 1O1-HBBH-5 | (—) | 3% |

NI=70.7° C.; Tc<−30° C.; Δn=0.090; η=17.2 mPa·s; Δ∈=−3.0; VHR-1=99.1%; VHR-2=97.2%; VHR-3=96.9%.

Example 14

| F2-HH-V | (1-1-1) | 5% |
|---|---|---|
| F2-HH-V3 | (1-1-1) | 5% |
| F3-HH-V | (1-1-1) | 7% |
| 3-BB(2F,3F)-O2 | (2-1-1) | 7% |
| 5-HHB(2F,3F)-O2 | (2-4-1) | 5% |
| V-HHB(2F,3F)-O2 | (2-4-1) | 5% |
| 2-HH1OB(2F,3F)-O2 | (2-7-1) | 7% |
| 3-HH1OB(2F,3F)-O2 | (2-7-1) | 5% |
| 4-HH1OB(2F,3F)-O2 | (2-7-1) | 5% |
| 2-HDhB(2F,3F)-O2 | (2-9-1) | 3% |
| 2-BB(2F,3F)B-3 | (2-12-1) | 7% |
| 3-HH-V | (3-1-1) | 15% |
| 5-HH-V | (3-1-1) | 5% |
| 5-HB-O2 | (3-2-1) | 3% |
| 1-BB-3 | (3-3-1) | 7% |
| 3-HHB-1 | (3-4-1) | 3% |
| 5-B(F)BB-2 | (3-7-1) | 3% |
| 5-B(F)BB-3 | (3-7-1) | 3% |

NI=72.2° C.; Tc<−30° C.; Δn=0.102; n=16.1 mPa·s; Δ∈=−3.2; VHR-1=99.0%; VHR-2=97.1%; VHR-3=96.5%.

Example 15

| F2-HH-V1 | (1-1-1) | 3% |
|---|---|---|
| F3-HH-V1 | (1-1-1) | 5% |
| 3-BB(2F,3F)-O2 | (2-1-1) | 5% |
| 4-BB(2F,3F)-O2 | (2-1-1) | 5% |
| V-HHB(2F,3F)-O2 | (2-4-1) | 7% |
| 2-HH1OB(2F,3F)-O2 | (2-7-1) | 7% |
| 3-HH1OB(2F,3F)-O2 | (2-7-1) | 5% |

-continued

| | | |
|---|---|---|
| 5-HDhB(2F,3F)-O2 | (2-9-1) | 3% |
| 3-HHB(2F,3CL)-O2 | (2-11-1) | 3% |
| 2-BB(2F,3F)B-3 | (2-12-1) | 5% |
| 5-H1OB(2F,3F)-O2 | (2) | 3% |
| 2-HH-3 | (3-1-1) | 5% |
| 3-HH-V | (3-1-1) | 17% |
| 3-HH-V1 | (3-1-1) | 5% |
| 1-BB-3 | (3-3-1) | 5% |
| 3-HHB-3 | (3-4-1) | 3% |
| V2-HHB-1 | (3-4-1) | 5% |
| 2-BB(F)B-3 | (3-6-1) | 4% |
| 2-BB(F)B-5 | (3-6-1) | 5% |

NI=76.0° C.; Tc<−30° C.; Δn=0.109; η=17.7 mPa·s; Δ∈=−3.4; VHR-1=99.2%; VHR-2=97.3%; VHR-3=96.7%.

The compositions according to Examples 6 to 15 have a lower minimum temperature and a larger negative dielectric anisotropy in comparison with the compositions according to Comparative Examples 1 and 2. Thus, the liquid crystal composition of the invention is so much superior in characteristics to the liquid crystal compositions shown in Patent literatures No. 1 and No. 2.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

The invention provides a liquid crystal composition satisfying at least one of characteristics such as a high maximum temperature of a nematic phase, a low minimum temperature of the nematic phase, a small viscosity, a large optical anisotropy, a large dielectric anisotropy, a large specific resistance, a high stability to ultraviolet light and a high stability to heat, or provides a liquid crystal composition having a suitable balance regarding at least two of the characteristics. A liquid crystal display device containing such a liquid crystal composition is applied as an AM device having a short response time, a large voltage holding ratio, a large contrast ratio, a long service life and so forth, and thus can be used for a liquid crystal projector, a liquid crystal television and so forth.

What is claimed is:

1. A liquid crystal composition that has a negative dielectric anisotropy and contains at least one compound selected from the group of compounds represented by formula (1) as a first component and at least one compound selected from the group of compounds represented by formula (2) as a second component:

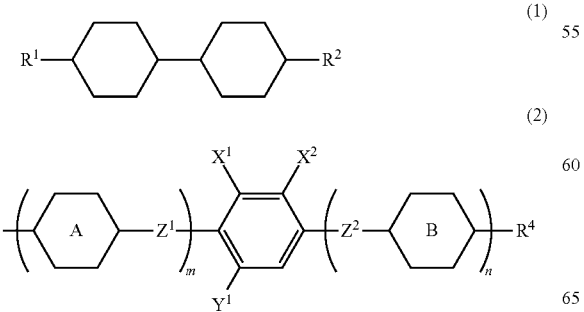

wherein $R^1$ is alkyl having 1 to 12 carbons in which one or two of hydrogen are replaced by fluorine; $R^2$, $R^3$ and $R^4$ are independently alkyl having 1 to 12 carbons, alkoxy having 1 to 12 carbons or alkenyl having 2 to 12 carbons; ring A and ring B are independently

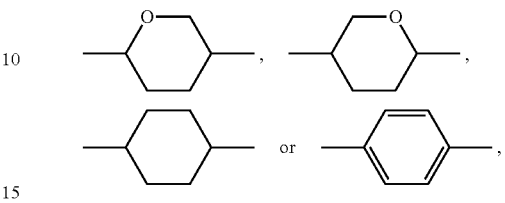

$X^1$ and $X^2$ are independently fluorine or chlorine; $Y^1$ is hydrogen or methyl; $Z^1$ and $Z^2$ are independently a single bond, ethylene, methyleneoxy or carbonyloxy; and m and n are independently 0, 1, 2 or 3, and a sum of m and n is 1, 2 or 3.

2. The liquid crystal composition according to claim 1, wherein the first component is at least one compound selected from the group of compounds represented by formula (1-1):

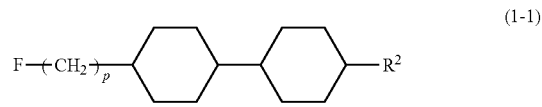

wherein $R^2$ is alkyl having 1 to 12 carbons, alkoxy having 1 to 12 carbons or alkenyl having 2 to 12 carbons; and p is an integer from 1 to 12.

3. The liquid crystal composition according to claim 1, wherein the second component is at least one compound selected from the group of compounds represented by formula (2-1) to formula (2-12):

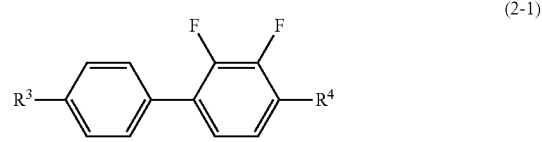

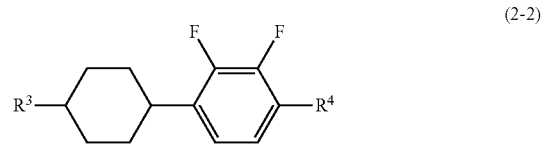

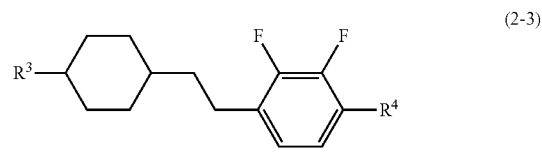

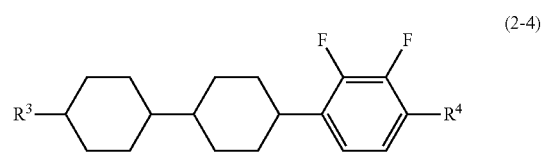

-continued (2-5)
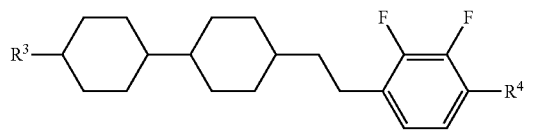

(2-6)
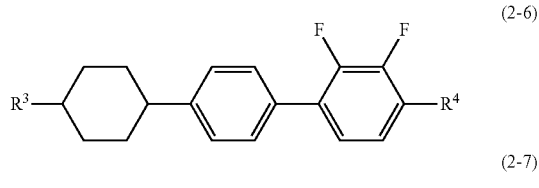

(2-7)
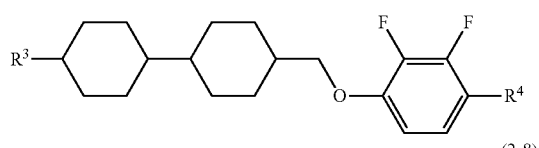

(2-8)
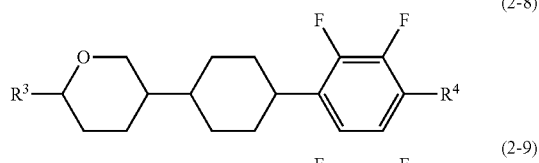

(2-9)
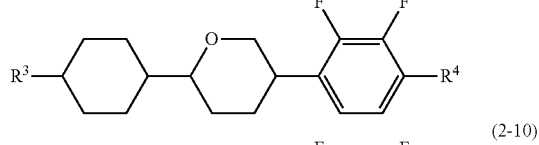

(2-10)
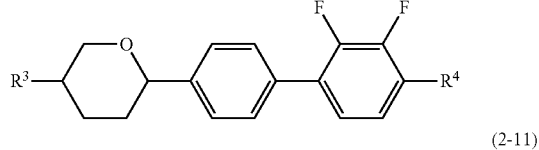

(2-11)
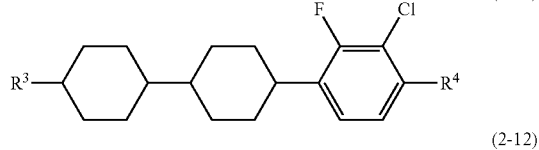

(2-12)
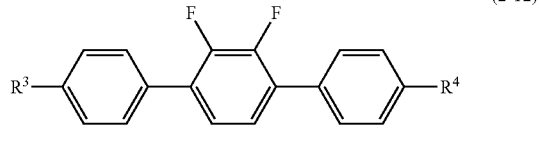

wherein $R^3$ and $R^4$ are independently alkyl having 1 to 12 carbons, alkoxy having 1 to 12 carbons or alkenyl having 2 to 12 carbons.

4. The liquid crystal composition according to claim 2, wherein the second component is at least one compound selected from the group of compounds represented by formula (2-4):

(2-4)
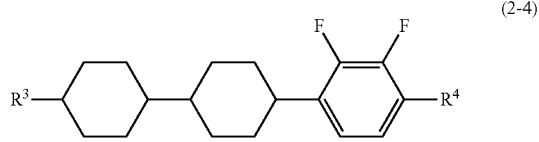

wherein $R^3$ and $R^4$ are independently alkyl having 1 to 12 carbons, alkoxy having 1 to 12 carbons or alkenyl having 2 to 12 carbons.

5. The liquid crystal composition according to claim 2, wherein the second component is at least one compound selected from the group of compounds represented by formula (2-7):

(2-7)
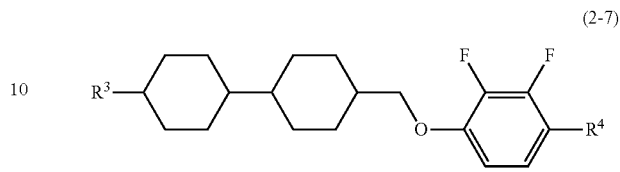

wherein $R^3$ and $R^4$ are independently alkyl having 1 to 12 carbons, alkoxy having 1 to 12 carbons or alkenyl having 2 to 12 carbons.

6. The liquid crystal composition according to claim 1, wherein a ratio of the first component is in the range of 5% by weight to 80% by weight and a ratio of the second component is in the range of 10% by weight to 95% by weight based on the total weight of the liquid crystal composition.

7. The liquid crystal composition according to claim 1, further containing at least one compound selected from the group of compounds represented by formula (3):

(3)
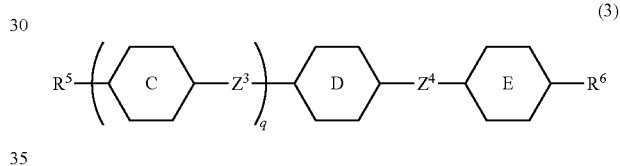

wherein $R^5$ and $R^6$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine; ring C, ring D and ring E are independently 1,4-cyclohexylene, 1,4-phenylene, 2-fluoro-1,4-phenylene or 3-fluoro-1,4-phenylene; $Z^3$ and $Z^4$ are independently a single bond, ethylene, methyleneoxy or carbonyloxy; and q is 0, 1 or 2.

8. The liquid crystal composition according to claim 7, wherein the third component is at least one compound selected from the group of compounds represented by formula (3-1) to formula (3-13):

(3-1)
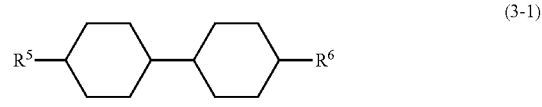

(3-2)
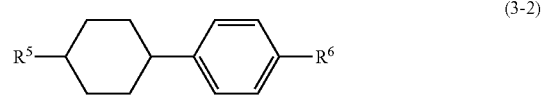

(3-3)
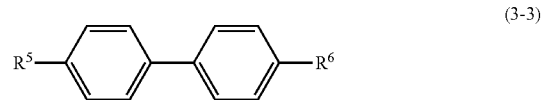

(3-4)
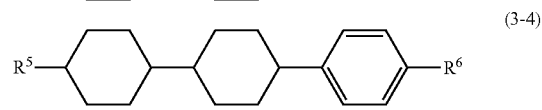

-continued

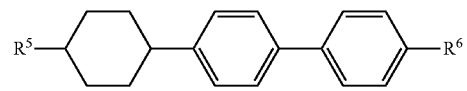
(3-5)

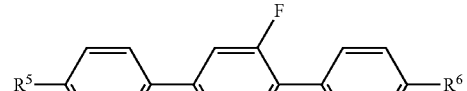
(3-6)

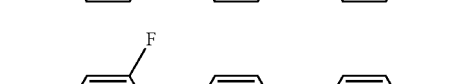
(3-7)

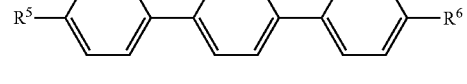
(3-8)

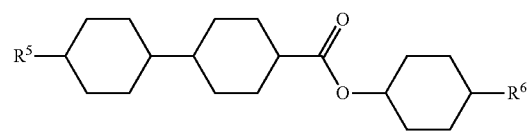
(3-9)

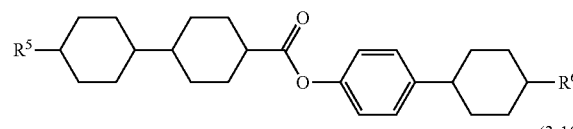
(3-10)

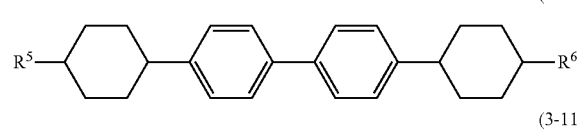
(3-11)

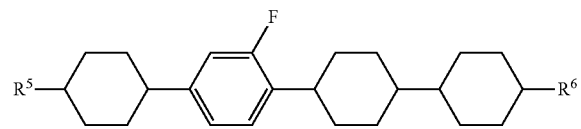
(3-12)

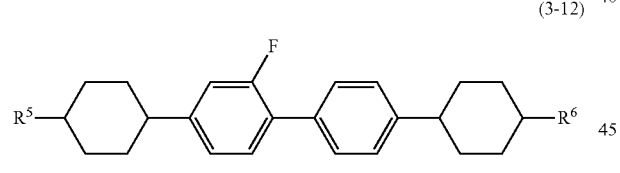
(3-13)

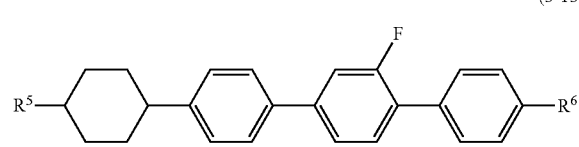

wherein $R^5$ and $R^6$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine.

9. The liquid crystal composition according to claim 7, wherein a ratio of the third component is in the range of 10% by weight to 80% by weight based on the total weight of the liquid crystal composition.

10. The liquid crystal composition according to claim 1, further containing at least one compound selected from the group of compounds represented by formula (4) as a fourth component:

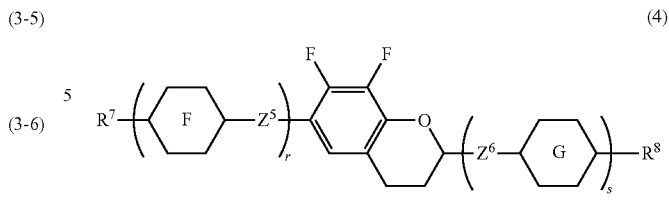
(4)

wherein $R^7$ and $R^8$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine; ring F and ring G are independently 1,4-cyclohexylene or 1,4-phenylene; $Z^5$ and $Z^6$ are independently a single bond, ethylene, methyleneoxy or carbonyloxy; r and s are independently 0, 1, 2 or 3, and a sum of r and s is 1, 2 or 3.

11. The liquid crystal composition according to claim 10, wherein the fourth component is at least one compound selected from the group of compounds represented by formula (4-1) to formula (4-5):

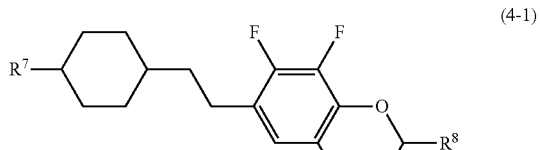
(4-1)

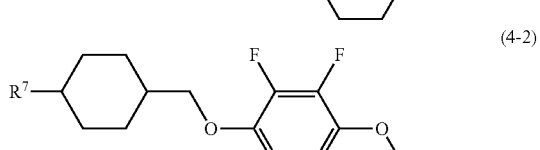
(4-2)

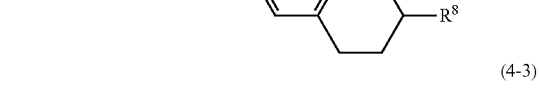
(4-3)

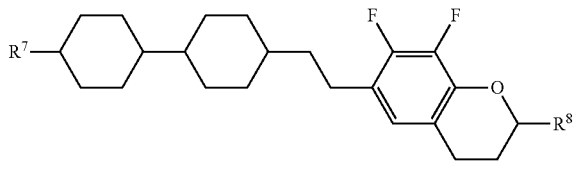
(4-4)

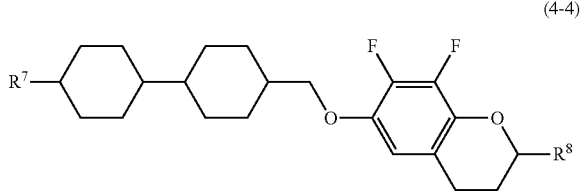
(4-5)

wherein $R^7$ and $R^8$ are independently alkyl having 1 to 12 carbons, alkoxy having 1 to 12 carbons or alkenyl having 2 to 12 carbons, or alkenyl having 2 to 12 carbons in which at least one hydrogen is replaced by fluorine.

12. The liquid crystal composition according to claim 10, wherein a ratio of the fourth component is in the range of 5% by weight to 40% by weight based on the total weight of the liquid crystal composition.

13. The liquid crystal composition according to claim 1, wherein a maximum temperature of a nematic phase is 70° C. or higher, an optical anisotropy (25° C.) at a wavelength of 589 nanometers is 0.08 or more, and a dielectric anisotropy (25° C.) at a frequency of 1 kHz is −2 or less.

14. A compound represented by formula (1-1-1):

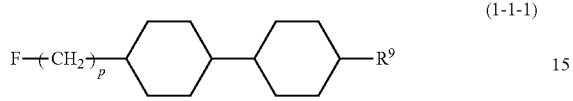

(1-1-1)

wherein p is an integer from 1 to 12; and $R^9$ is alkenyl having 2 to 3 carbons.

15. A liquid crystal display device, containing the liquid crystal composition according to claim 1.

16. The liquid crystal display device according to claim 15, wherein an operating mode in the liquid crystal display device is a VA mode, an IPS mode, an FFS mode or a PSA mode, and a driving mode in the liquid crystal display device is an active matrix mode.

* * * * *